(12) United States Patent
Simpson

(10) Patent No.: US 6,440,129 B1
(45) Date of Patent: *Aug. 27, 2002

(54) ELECTRODE HAVING NON-JOINED THERMOCOUPLE FOR PROVIDING MULTIPLE TEMPERATURE-SENSITIVE JUNCTIONS

(75) Inventor: John A. Simpson, Carlsbad, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,196

(22) Filed: Feb. 10, 2000

Related U.S. Application Data

(63) Continuation of application No. 09/072,853, filed on May 5, 1998, now Pat. No. 6,045,550.

(51) Int. Cl.[7] ............................................. A61B 18/18
(52) U.S. Cl. ........................ 606/42; 607/102; 600/549
(58) Field of Search ........................ 606/31–35, 41, 606/42, 45–50; 607/101, 102; 600/374, 549

(56) References Cited

U.S. PATENT DOCUMENTS 4,411,266 A * 10/1983 Cosman ........................ 606/50
4,966,597 A * 10/1990 Cosman ........................ 606/50
5,688,266 A * 11/1997 Edwards et al. ............... 606/31
5,893,885 A * 4/1999 Webster, Jr. .................. 67/122

OTHER PUBLICATIONS

ISHM '87 Proceedings "Taming Thermocouple Voltages in Microelectronics" by Roy Chapel, pp. 104–112.
"The Thermocouple", Omega Catalog, vol. 27, pp. Z9–Z20.

* cited by examiner

Primary Examiner—Michael Peffley
(74) Attorney, Agent, or Firm—Fulwider Patton Lee & Utecht, LLP

(57) ABSTRACT

The non-joined thermocouple electrode configuration, for use in an RF ablation catheter for ablating biological tissue such as cardiac tissue, allows temperature to be monitored at two locations of a band electrode while only using a single pair of thermocouple wires. The thermocouple wires are connected to the electrode at separate locations. They preferably are formed of metallic materials having Seebeck coefficients that are substantially equal in magnitude but opposite in sign relative to the electrode material connecting the two. In the case of a band electrode, the two thermocouple wires are preferably spaced apart on the band electrode so that the first junction contacts the tissue having a first temperature and the second junction contacts circulating blood having a second temperature. The voltage across the thermocouple wires provides an indication of the average of the two junctions temperatures so that by monitoring the temperature of the blood, the temperature of the first junction can be determined from this average temperature.

18 Claims, 16 Drawing Sheets

FIG. 8A

| FIG. 8B | FIG. 8C | FIG. 8D |
|---|---|---|
| | | FIG. 8E |

FIG. 8B

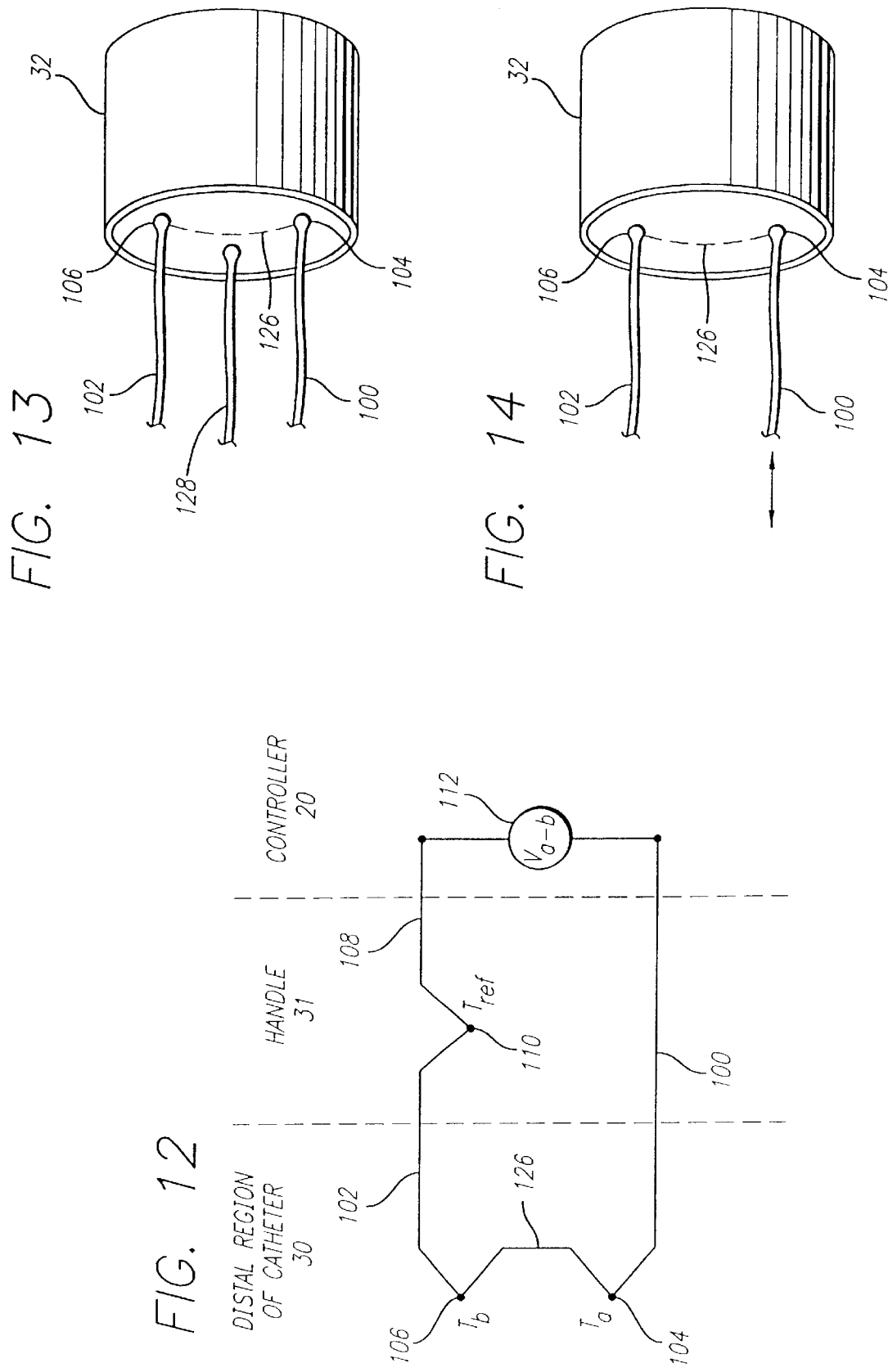

ELECTRODE HAVING NON-JOINED THERMOCOUPLE FOR PROVIDING MULTIPLE TEMPERATURE-SENSITIVE JUNCTIONS

RELATED APPLICATIONS

This is a continuation of application Ser. No. 09/072,853, filed May 5, 1998 now U.S. Pat. No. 6,645,550.

BACKGROUND OF THE INVENTION

The invention relates generally to an electrophysiological ("EP") apparatus and method for providing energy to biological tissue, and more particularly, to a catheter having an electrode with a non-joined thermocouple for providing multiple temperature-sensitive junctions on the electrode.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

During ablation, portions of the electrodes are typically in contact with the blood, so that it is possible for clotting and boiling of blood to occur if those electrodes reach an excessive temperature. Both of these conditions are undesirable. Clotting is particularly troublesome at the surface of the catheter electrode because the impedance at the electrode rises to a level where the power delivery is insufficient to effect ablation. The catheter must be removed and cleaned before the procedure can continue. Additionally, too great a rise in impedance can result in sparking and thrombus formation within the heart, both of which are also undesirable.

Further, too great a temperature at the interface between the electrode and the tissue can cause the tissue to reach a high impedance which will attenuate and even block the further transmission of RF energy into the tissue thereby interfering with ablation of tissue at that location.

Even though no significant amount of heat is generated in the electrodes themselves, adjacent heated endocardial tissue heats the electrodes via heat conduction through the tissue. As mentioned above, part of the active electrode will be in contact with the blood in the heart and if the electrode temperature exceeds 90–100°, it can result in blood boiling and clotting on the electrode. The application of RF energy must then be stopped. However, shutting the RF generator off due to the temperature rise may not allow sufficient time to complete the entire ablation procedure. Providing an ablation electrode capable of applying higher amounts of power for a longer period of time to ablate the damaged tissue to an acceptable depth is a goal of current ablation catheter electrode design. It has been found that higher power for longer time periods results in a higher probability of success of the ablation procedure.

To avoid clotting and blood boiling, RF ablation catheters for cardiac applications typically provide temperature feedback during ablation via a temperature sensor such as a thermocouple. In its simplest form, a thermocouple consists of two dissimilar metals joined together at one end called a "bead" or junction, such as a conventional copper/constantan type "T" thermocouple. When the junction is heated a thermoelectric potential arises and can be measured across the unconnected ends. This is also known as the thermoelectric or Seebeck effect. This voltage is proportional to the temperature difference between the junction and the non-joined ends.

A conventional RF ablation catheter typically has a single tip electrode and a single temperature sensor mounted along the centerline of the tip electrode where temperature readings are not affected by the rotational orientation of the catheter. Although a temperature gradient typically exists in tip electrodes, wherein the electrode is hottest at the tissue interface and coolest on the opposite side which is in contact with circulating blood, the centerline sensor provides a moderate output by which it can be determined whether the temperature of the tissue contacted by the electrode is being raised sufficiently, and whether a therapeutic lesion is being generated.

In the case where a catheter has a band electrode, such as for the treatment of atrial fibrillation by the ablation of tissue, a single temperature sensor mounted to the band may not provide the temperature of the tissue contacting the band electrode. Typically the side of the band which is in direct contact with the tissue becomes significantly hotter than the rest of the band electrode that is cooled by the blood flow. Thus, the temperature reading can be dramatically influenced by the rotational orientation of the catheter during RF ablation. If the band is oriented so that the single temperature sensor is not in contact with the tissue during the application of ablation energy, not only would there be a time lag in the sensor reaching the tissue temperature, but due to the effect of the cooling blood flow, the sensor reading may never approach the actual tissue temperature.

To overcome the effect that the rotation orientation of the band electrode has on temperature sensing, two thermocouples, positioned at different locations of the band electrode, may be used. A theory is that having a sensor in contact with tissue is more likely. While attachment of multiple temperature sensors to the band electrode can result in a higher probability of sensing the actual tissue interface temperature, this also increases the number of wires occupying space within the catheter. As is well appreciated by those skilled in the art, an increase in the number of internal wires could mean an undesirable increase in catheter diameter to accommodate those wires. Conventional types of thermocouples each require a thermocouple wire pair. Two thermocouples at each band electrode would result in four wires per band electrode so that the use of multiple temperature sensors may not be practical, particularly where the catheter carries multiple band electrodes that require temperature monitoring.

The larger the catheter, the more traumatic it is to the patient. Also, the more difficult it may be to negotiate the patient's vessels to position the catheter at the desired location in the heart. It is desirable to provide a catheter with as small a diameter as possible. A limiting factor in reducing the size of the catheter is the amount of devices and leads that must be carried inside the catheter. In the case of a catheter having ten band electrodes with two thermocouple temperature sensors at each electrode, a total of fifty wires would be necessary; one power wire for each electrode and two wires for each thermocouple. The size of fifty wires inside a catheter can be significant, causing an increased diameter of the catheter. Yet it is desirable to retain the electrodes and the associated temperature sensors so that more precise control over the energy applied to the biological tissue can be effected. Thus, it would be desirable to reduce the number of wires within a catheter, yet retain the same functionality.

Hence, those skilled in the art have recognized a need for a minimally invasive ablation apparatus that is capable of controlling the flow of current through a biological site so that lesions with controllable surface and depth characteristics may be produced and the ablation volume thereby controlled. Additionally, a need has been recognized for providing an electrode with multiple temperature sensors for providing reliable electrode/tissue interface temperature readings substantially independent of the rotational orientation of the catheter but with a reduced number of sensor leads. Similarly, a need has been recognized for a method for reliably determining the electrode/tissue interface temperature readings substantially independent of the rotational orientation of the catheter but with a reduced number of sensor leads The invention fulfills these needs and others.

SUMMARY OF THE INVENTION

Briefly, and in general terms, the invention is directed to an apparatus and a method for controlling the application of energy to a biological site using a catheter having an energy application device, e. g., an electrode, and a sensor device e. g., a thermocouple, at its distal end for providing multiple temperature-sensitive locations on the electrode with a reduced number of leads.

In a first aspect, an apparatus includes a catheter having an electrode formed of a first metallic material. The electrode is disposed at a distal end of the catheter, the distal end adapted to be positioned so that the electrode is located proximal the biological tissue. The catheter also includes a first electrically conductive member formed of second metallic material, the first member is connected to the electrode at a first junction. Also included is a second electrically conductive member formed of a third metallic material; the second member is connected to the electrode at a second junction. The first, second and third metallic materials are chosen such that when the first and second junctions are at different temperatures a voltage output is produced across the electrode proportional to the temperature difference between the two junctions.

By selecting the first, second, and third metallic materials so that a voltage is produced which is proportional to the temperature average of the two points on the electrode, the present invention allows for the determination of the temperature at two distinct points on the electrode using only one pair of electrically conductive members. Thus the number of wires required to fit within a catheter is reduced, thereby allowing for a reduction in the catheter size.

In a detailed aspect of the invention, the first and second junctions are spaced apart on the electrode such that the voltage output is indicative of a temperature which is the average of the first and second junction temperatures. In a further detailed aspect, the first and second junctions are spaced apart on the electrode such that when the electrode is located proximal the biological tissue, one of the junctions is positioned near the electrode/tissue interface while the other junction is positioned in the biological fluid. In another detailed aspect, the electrode comprises a band electrode and the first and second junctions are located on the band electrode approximately 180 degrees apart around the band electrode inner circumference. In yet another detailed aspect, the second and third metallic materials are metallic materials having Seebeck coefficients relative to the first metallic material that are substantially equal in magnitude but opposite in sign.

In another detailed aspect of the invention, the apparatus further includes a power control system which is adapted to provide power for the electrode and to control the duty cycle of the power with the duty cycle having an on-period and an off-period within a duty cycle time frame. The power control system is further adapted to monitor voltage output produced across the electrode. In a further detailed aspect, the power control system controls the duty cycle of the power in response to the voltage output. In another detailed aspect, the catheter comprises a plurality of electrodes at its distal end, each electrode having a first and second electrically conductive member connected at a first and second junction and the power control system is further adapted to provide power to each of the electrodes wherein the power is selected such that at least two electrodes have voltage levels that differ from each other so that current flows between the two electrodes. In yet more detailed aspects, the power control system provides power with different phase angles to at least two of the electrodes; the power differs in phase by an amount greater than zero degrees but less than 180 degrees; and the power differs in phase by an amount approximately equal to 132 degrees.

In a further detailed aspect, the invention includes a backplate adapted to be positioned proximal the biological site so that the biological site is interposed between the electrodes and the backplate. The power control system is adapted to provide power to the electrodes wherein the power is selected such that at least one electrode has a voltage level that differs from the backplate so that current flows between at least one electrode and the backplate.

In yet another aspect, the invention is an apparatus for delivering energy to biological tissue located in a biological structure in which biological fluids flow past the tissue. The apparatus includes a catheter having a plurality of band electrodes formed of a first metallic material, the band electrodes disposed at a distal end of the catheter, the distal end is adapted to be positioned so that at least one of the band electrodes is located proximal the biological tissue. Also included is a plurality of first electrically conductive members formed of second metallic material, one first member is connected to one band electrode at a first junction. Further included is a plurality of second electrically conductive members formed of a third metallic material, one second member is connected to one band electrode at a second junction. The first, second and third metallic materials are chosen such that when the first and second junctions are at different temperatures a voltage output is produced across the electrode proportional to the temperature difference between the two junctions. Also included is a power control system adapted to provide power to each band electrode and to control the duty cycle of the power with the duty cycle having an on-period and an off-period within a duty cycle time frame. The power control system is further adapted to monitor voltage output produced across each electrode. Still further included is a backplate adapted to be positioned proximal the biological tissue so that the biological tissue is interposed between the electrodes and the backplate.

In a further aspect, a method for monitoring the temperature at the interface between an electrode and biological tissue during ablation of the biological tissue includes the step of positioning a catheter proximal the biological tissue to be ablated. The catheter has an electrode formed of a first metallic material and first and second electrically conductive members connected to the electrode at a first junction and a second junction, respectively. The first and second electrically conductive members are formed of second and third metallic materials, respectively, such that when the two junctions are at different temperatures, a voltage output is produced across the electrode proportional to the temperature average of the two junctions. The first and second electrically conductive members are spaced apart on the electrode. The method further includes the steps of positioning the electrode against the tissue for ablation so that a portion of the electrode is available for contact with the fluids in the biological structure and measuring the voltage output across the electrode as an indication of a temperature which is the average of the two junction temperatures.

In a detailed aspect, the method further includes the steps of placing the first junction in contact with the biological tissue and the second junction in contact with the biological fluid; measuring the temperature of the biological fluid; and determining the temperature of the first junction from the average temperature. In another detailed aspect of the invention, the electrode is a band electrode and the method further comprises the steps of placing the first junction in contact with the biological tissue and the second junction approximately 180° away from the first unction around the band electrode circumference; measuring the temperature of the biological fluid; and determining the temperature of the first junction from the average temperature.

These and other aspects and advantages of the invention will become apparent from the following detailed description and the accompanying drawings, which illustrate by way of example the features of the invention.

BRIEF DESCRIPTION OF THE DRAWINGS

FIGS. 2-1 and 2-2 form a block diagram presenting more detail of a power control system in accordance with aspects of the invention, showing phase angle control, duty cycle control, and impedance and temperature monitoring;

FIGS. 8A, 8B, 8C, 8D, and 8E are schematic diagrams of an embodiment of a power control system in accordance with aspects of the invention with FIG. 8A showing how FIGS. 8B, 8C, 8D and 8E are related;

FIG. 12 is a schematic diagram of a non-joined thermocouple with thermocouple legs attached to a wire simulating a portion of a band electrode according to the principles of the invention;

FIG. 13 is a diagram of a single band electrode showing the connection of thermocouple wires in accordance with one aspect of the invention where a separate wire conducts ablation energy to the electrode;

FIG. 14 is a diagram of a single band electrode showing the connection of thermocouple wires in accordance with one aspect of the invention where one of the wires also conducts ablation energy to the electrode;

DETAILED DESCRIPTION OF PREFERRED EMBODIMENTS

Figure 1:
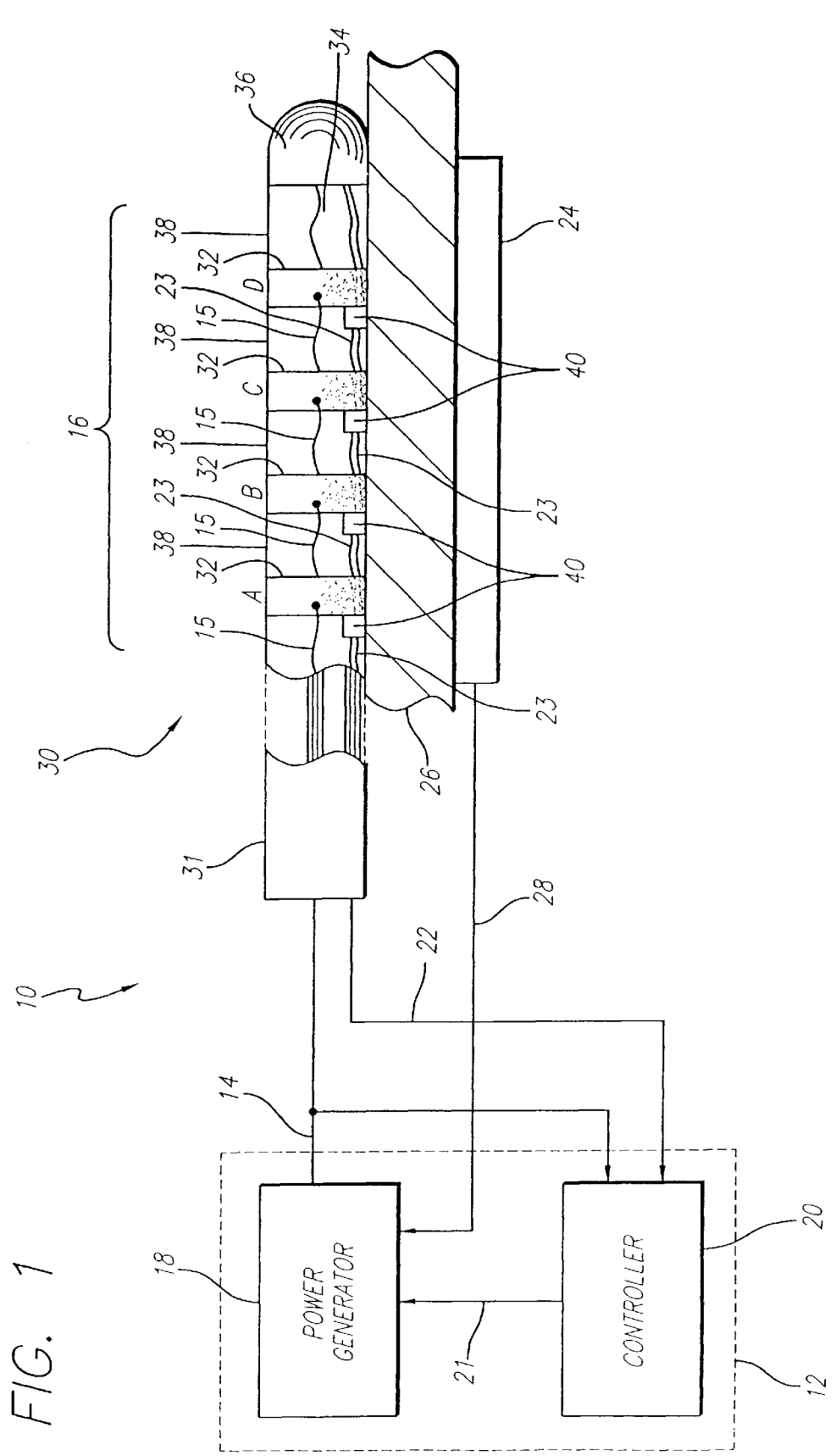
FIG. 1 is a schematic diagram of an ablation apparatus including a power control system, electrode device and backplate.

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive 14 to an electrode device 16. The power control system 12 comprises a power generator 18 that may have any number of output channels through which it provides the power 14. The operation of the power generator 18 is controlled by a controller 20 which outputs control signals 21 to the power generator 18. The controller 20 monitors the power 14 provided by the power generator 18. In addition, the controller 20 also receives temperature signals 22 from the electrode device 16. Based on the power 14 and temperature signals 22 the controller 20 adjusts the operation of the power generator 18. A backplate 24 is located proximal to the biological site 26 opposite the site from the electrode device 16, and is connected by a backplate wire 28 to the power generator 18. The backplate 24 is set at the reference level to the power provided electrodes, as discussed in detail below.

The electrode device 16 is typically part of a steerable EP catheter 30 capable of being percutaneously introduced into a biological site 26, e. g., the atrium or ventricle of the heart. The electrode device 16 is shown in schematic form with the components drawn to more clearly illustrate the relationship between the components and the relationship between the components and the power control system 12. In this embodiment, the catheter 30 comprises a distal segment 34 and a handle 31 located outside the patient. A preferred embodiment of the electrode device 16 includes twelve band electrodes 32 arranged in a substantially linear array along the distal segment 34 of the catheter 30. The electrode device 16 may include a tip electrode 36. (For clarity of illustration, only four band electrodes 32 are shown in the figures although as stated, a preferred embodiment may include many more.) The band electrodes 32 are arranged so that there is space 38 between adjacent electrodes. In one configuration of the electrode device 16, the width of the band electrodes 32 is 3 mm and the space 38 between the electrodes is 4 mm. The total length of the electrode device 16, as such, is approximately 8 cm.

The arrangement of the band electrodes 32 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter 30 and also lessens the size of the catheter.

The band electrodes 32 are formed of a material having a significantly higher thermal conductivity than that of the biological tissue 26. Possible materials include silver, copper, gold, chromium, aluminum, molybdenum, tungsten, nickel, platinum, and platinum/10% iridium. Because of the difference in thermal conductivity between the electrodes 32 and the tissue 26, the electrodes 32 cool off more rapidly in the flowing fluids at the biological site. The power supplied to the electrodes 32 may be adjusted during ablation to allow for the cooling of the electrodes while at the same time allowing for the temperature of the tissue to build up so that ablation results. The electrodes 32 are sized so that the surface area available for contact with fluid in the heart, e. g., blood, is sufficient to allow for efficient heat dissipation from the electrodes to the surrounding blood. In a preferred embodiment, the electrodes 32 are 7 French (2.3 mm in diameter) with a length of 3 mm.

The thickness of the band electrodes 32 also affects the ability of the electrode to draw thermal energy away from the tissue it contacts. In the present embodiment, the electrodes 32 are kept substantially thin so that the electrodes effectively draw energy away from the tissue without having to unduly increase the outer diameter of the electrode. In a preferred embodiment of the invention, the thickness of the band electrodes is 0.05 to 0.13 mm (0.002 to 0.005 inches).

Associated with the electrode device 16 are temperature sensors 40 for monitoring the temperature of the electrode device 16 at various points along its length. In one embodiment, each band electrode 32 has a temperature sensor 40 mounted to it. Each temperature sensor 40 provides a temperature signal 22 to the controller 20 which is indicative of the temperature of the respective band electrode 32 at that sensor. In another embodiment of the electrode device 16 a temperature sensor 40 is mounted on every other band electrode 32. Thus for a catheter having twelve electrodes, there are temperature sensors on six electrodes. In yet another embodiment of the electrode device 16 every other electrode has two temperature sensors 40. In FIG. 1, which shows an embodiment having one temperature sensor for each electrode, there is shown a single power lead 15 for each electrode 32 to provide power to each electrode for ablation purposes and two temperature leads 23 for each temperature sensor 40 to establish the thermocouple effect.

Figures 1, 2:
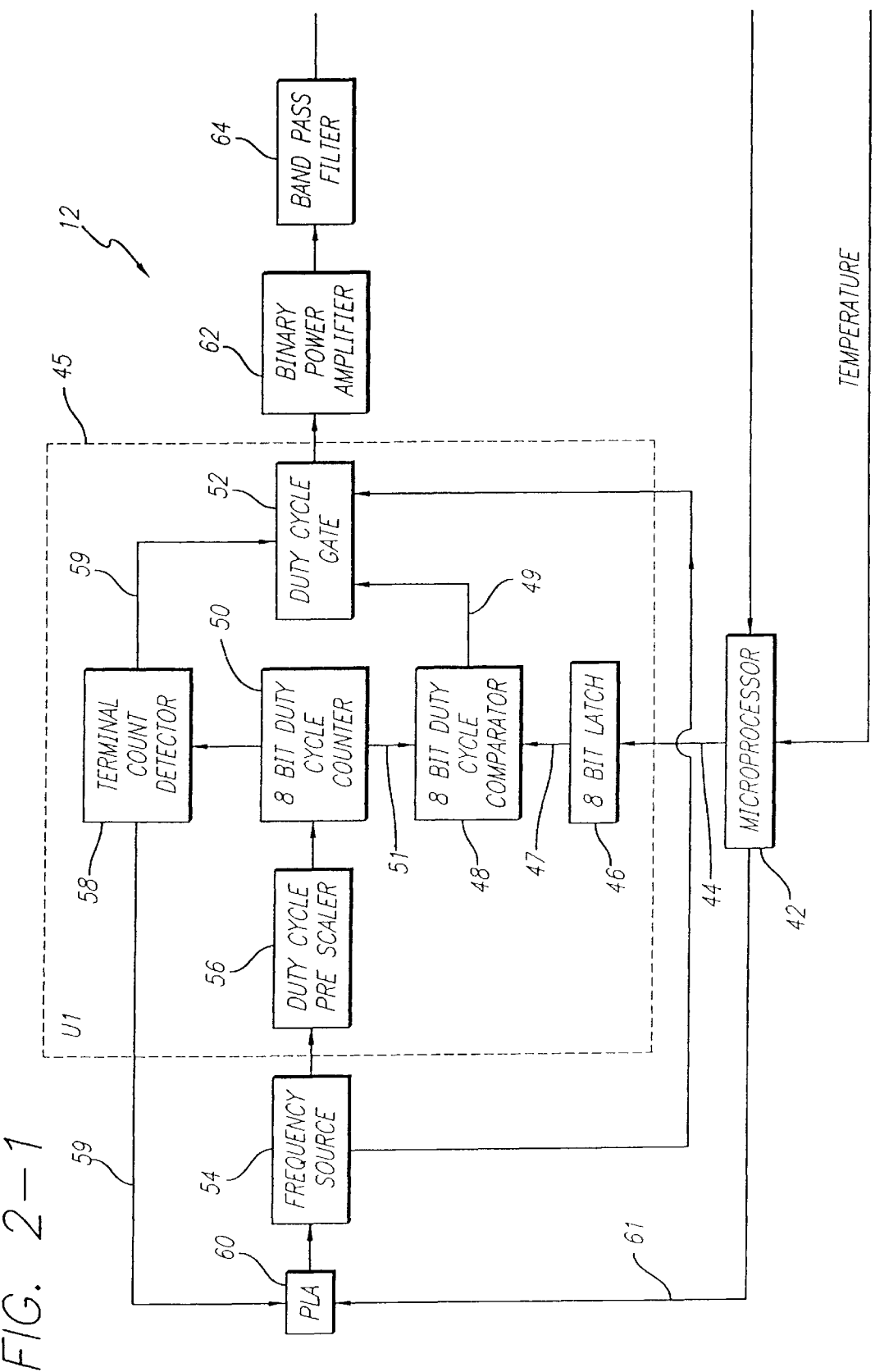
Figure 2:
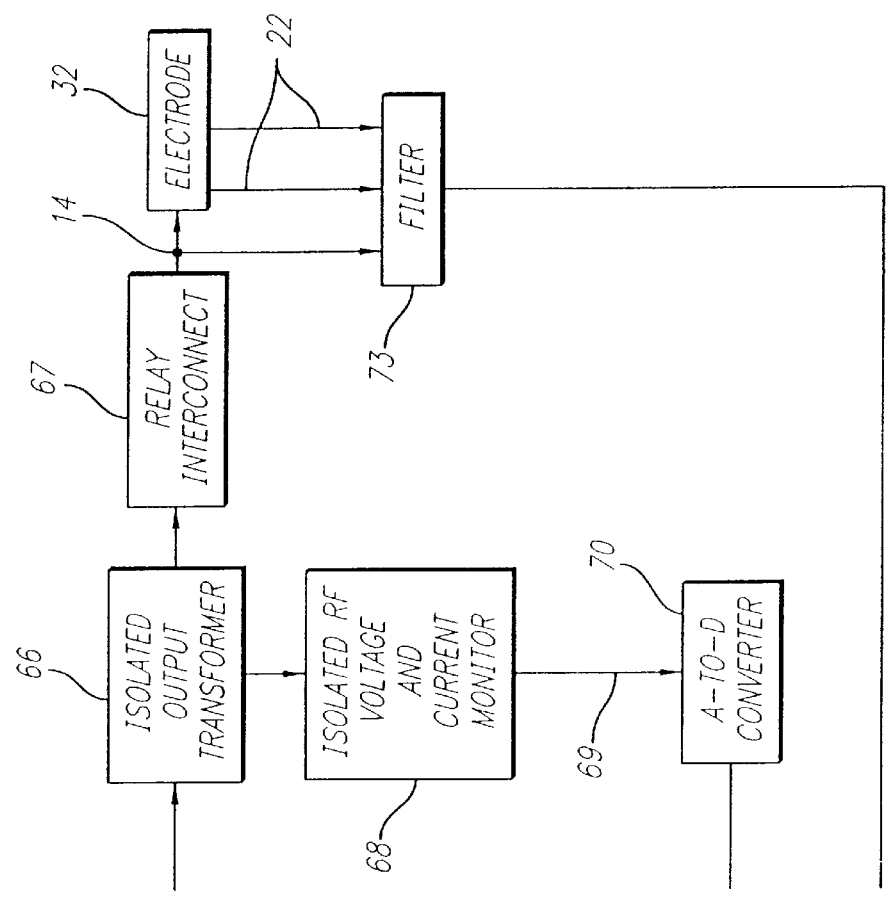

Turning now to FIGS. 2-1 and 2-2, a block diagram of an ablation apparatus 10 and method in accordance with aspects of the invention is presented. In FIGS. 2-1 and 2-2, a single channel of the power control system 12 is depicted. This channel controls the application of power to a single electrode 32. As will be discussed in relation to other figures, a channel may control a plurality or group of electrodes. In FIG. 2-1, a microprocessor 42, which is part of the controller 20 (FIG. 1), provides a duty cycle control signal 44 to a duty cycle generator 45. In this case, the duty cycle generator ("DCG") 45 receives the control signal 44 by an 8-bit latch 46. The latch 46 provides an 8-bit signal 47 to a duty cycle comparator 48. The comparator 48 compares the 8-bit signal 47 to a count from an 8-bit duty cycle counter 50 and if the count is the same, provides a duty cycle off signal 49 to the duty cycle gate 52. The gate 52 is connected to a frequency source ("FS") 54, such as an oscillator that produces 500 kHz. When the gate 52 receives the duty cycle off signal 49 from the comparator 48, it stops its output of the frequency source signal through the gate and no output exists.

At a frequency of 500 kHz, an 8-bit control has a period or time frame of 0.5 msec. At a fifty-percent duty cycle, the electrode is in the off period only 0.25 msec. To allow for greater cooling of the electrode, the period or time frame 78 (FIG. 6) is lengthened by use of a prescalar 56 interposed between the frequency source 54 and the counter 50. In one embodiment, the prescalar 56 lengthens the period to 4 msec thus allowing for a 2 msec off period during a fifty-percent duty cycle. This results in a sufficient cooling time for the very thin band electrodes discussed above. Other lengths of the period may be used depending on the circumstances. It has been found that a ten percent duty cycle is particularly effective in ablating heart tissue. The combination of the application of high peak power, a ten percent duty cycle, the use of high thermal conductivity material in the band electrodes, and fluids flowing past the band electrodes which have a cooling effect on the electrodes result in a much more effective application of power to the tissue. Ablation occurs much more rapidly.

A terminal count detector 58 detects the last count of the period and sends a terminal count signal 59 to the gate 52 which resets the gate for continued output of the frequency source signal. This then begins the on period of the duty cycle and the counter 50 begins its count again. In one preferred embodiment, the duty cycle is set at fifty percent and the 8-bit latch is accordingly set to 128. In another embodiment, the duty cycle is set at ten percent.

A programmable logic array ("PLA") 60 receives phase control signals 61 from the microprocessor 42 and controls the phase of the frequency source 54 accordingly. In one embodiment, the PLA 60 receives the terminal count signal 59 from the terminal count detector 58 and only permits phase changes after receiving that terminal count signal.

The output signal from the gate 52 during the on period of the duty cycle is provided to a binary power amplifier ("BPA") 62 that increases the signal to a higher level, in this case, 24 volts. The amplified signals are then filtered with a band pass filter ("BPA") 64 to convert the somewhat square wave to a sine wave. The band pass filter 64 in one embodiment is centered at 500 kHz. The filtered signal is then provided to an isolated output transformer ("IOT") 66 that amplifies the signal to a much higher level, for example 350 volts peak-to-peak. This signal is then sent to a relay interconnect ("RI") 67 before it is provided as a power output signal OUTn 14 to an electrode 32 at the biological site to cause ablation.

The power output signal 14 from the isolated output transformer 66 is monitored in one embodiment to determine the impedance at the electrode 32. In the embodiment shown in FIGS. 2-1 and 2-2, a voltage and current monitor ("VCM") 68 is used. The monitor signal 69 is converted to digital form by an A-to-D converter ("ADC") 70 and provided to the microprocessor 42. As previously mentioned, some or all of the electrodes 32 may include a temperature sensor 40 (FIG. 1) that provides temperature signals 22 (FIG. 2-2) which are used to determine the temperature at the electrode 32. In one embodiment of the invention, the power 14, in conjunction with the temperature signals 22, are used to determine the temperature at the electrode 32. Both the temperature signals 22 and the power 14 pass through a temperature filter ("FL") 73 before being sent to the microprocessor 42. In the alternative, the temperature filter 73 is contained in a printed circuit board separate from the controller 20 and contains its own processor. In either case, the filter 73 filters out any RF noise present in the power 14 so that the signal may be used for temperature monitoring purposes. In another embodiment, the microprocessor monitors the power 14 and temperature signals 22 only during the off periods of the power 14 duty cycle. Accordingly, negligible RF noise is present in the power line and filtration is not necessary. In either embodiment, the microprocessor 42 may alter the duty cycle of the power 14 in response to either or both of the impedance or temperature signals.

In a manual arrangement, the temperature sensed and/or the determined impedance may be displayed to an operator. The operator in response may then manually control the duty cycle or other power parameters such as by rotating a knob mounted on a front panel of an instrument. In the case of a multiple channel instrument and catheter, as discussed below, multiple knobs may be provided in this manual arrangement for control over each channel.

Figure 3:
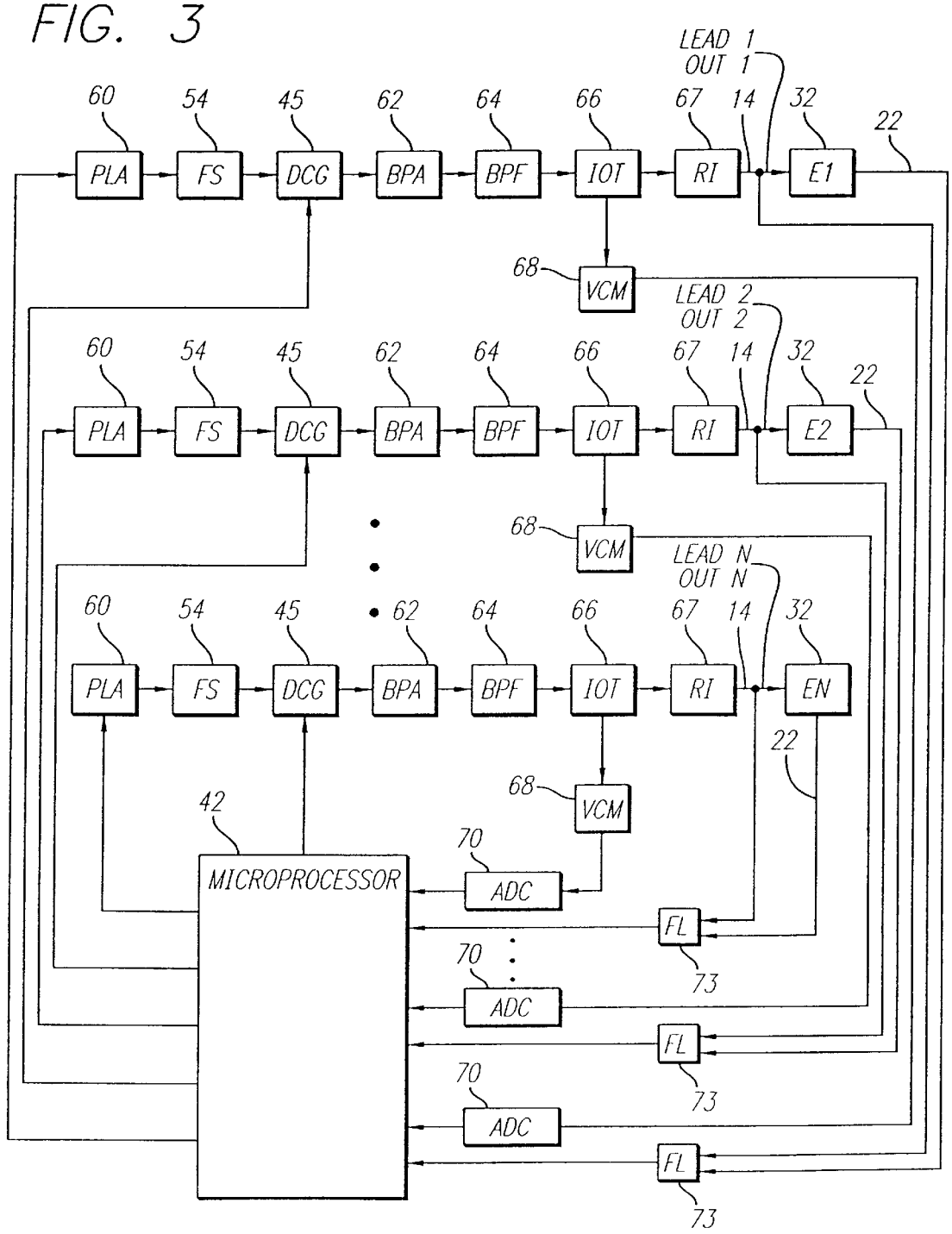
FIG. 3 is a diagram of a multi-channel ablation apparatus in accordance with aspects of the invention wherein a single microprocessor controls the phase angle and duty cycle of each channel individually.

Referring now to FIG. 3, a multiple channel ablation apparatus is shown. Although only three complete channels are shown, the apparatus comprises many more as indicated by the successive dots. Those channels are not shown in FIG. 3 to preserve clarity of illustration. By providing different voltage levels between two electrodes 32 in an array, current flows between those electrodes in a bipolar electrode approach. By setting the backplate 24 (FIG. 1) at a voltage level different from at least one of those electrodes 32, current flows between that electrode and the backplate. By controlling the voltage levels among the three (two electrodes and backplate), the current flow through the biological site 26 can be more precisely controlled. One technique for setting different voltage levels between the electrodes 32 is to maintain a phase difference between them in an AC approach. By setting the backplate 24 at the reference level, current flows between the electrodes 32 and the backplate.

The single microprocessor 42, which again is part of the controller 20 (FIG. 1), controls the duty cycle and the phase of each channel individually in this embodiment. Each channel shown comprises the same elements and each channel produces its own power output signal 14 (OUT1, OUT2, through OUTn where "n" is the total number of channels) on respective electrode leads (LEAD 1, LEAD 2, through LEAD n where "n" is the total number of leads) to the electrodes 32. This multi-channel approach permits more individual control over each electrode. For example, the duty cycle of the power applied to each electrode can be individually controlled. One electrode may have a ten percent duty cycle while another has a thirty percent duty cycle.

Figure 4:
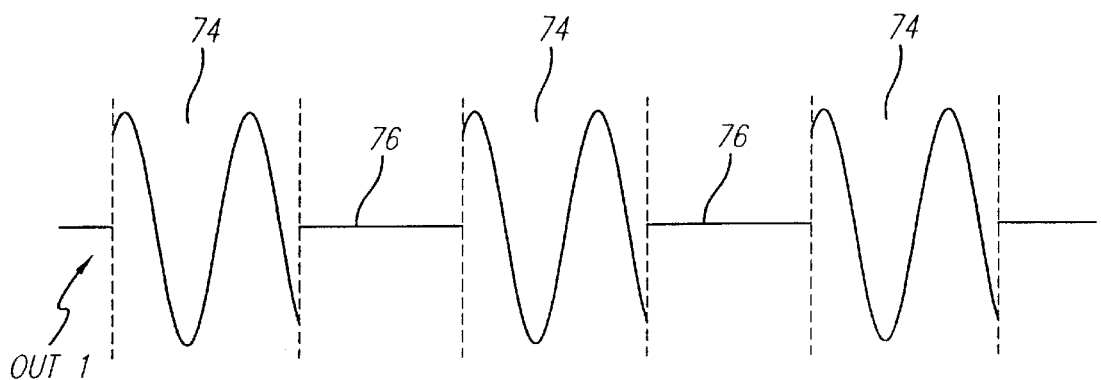
FIG. 4 depicts a first powerwaveform having a first phase angle and alternating instances of peak power and very low power.
Figure 5:
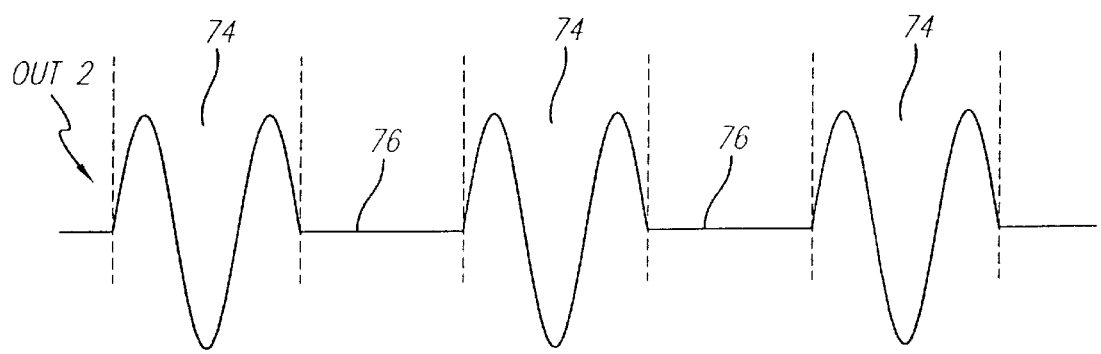
FIG. 5 depicts a second power waveform having a second phase angle different from the first phase angle and alternating instances of peak power and very low power.
Figure 6:
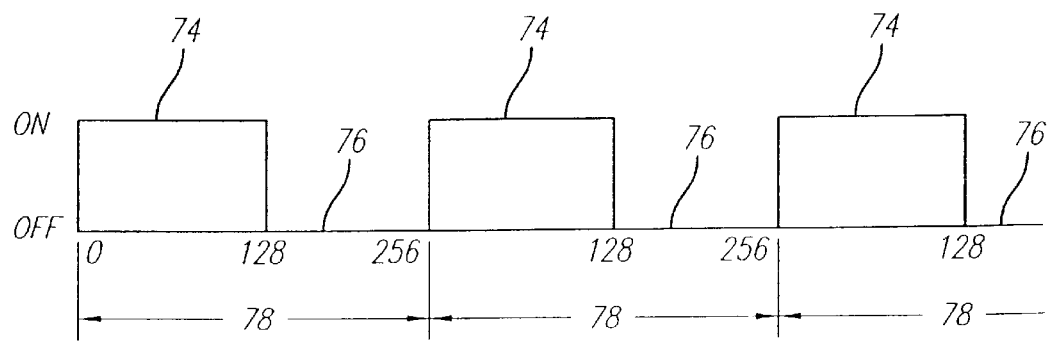
FIG. 6 presents a time frame (TF) diagram showing a fifty-percent duty cycle.

Referring now to the first and second output signals OUT1 and OUT2 of FIG. 3, the signals, as shown in FIGS. 4, 5, and 6, have alternating instances of peak power i. e., "on" periods 74, and very low power 76, i. e., "off" periods. Typically, the output power 14 is a 500 kHz sine wave. In FIGS. 4 and 5, the number of cycles of the sine wave contained within one on period 74 has been substantially reduced in the drawing to emphasize the phase difference between the first and second output signals OUT1, OUT2. Preferably, the voltage of each power signal 14 during an off period 76 is substantially zero and during an on period 74 is approximately 350 volts peak-to-peak.

The power OUT1 and OUT2 also have a variable duty cycle for controlling the length of the on period 74 and the off-period 76 within a time frame 78 (see FIG. 6). The duty cycle is the ratio of the length of the on period 74 to the length of the entire time frame 78. The effective power is the peak power times the duty cycle. Thus, a signal having a peak power of 100 watts and a 50% duty cycle has an effective power of 50 watts.

Figure 7A:
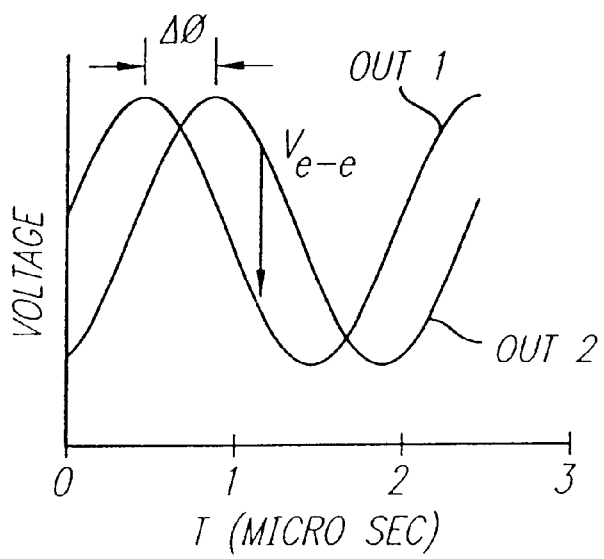
FIG. 7A depicts the phase relationship and voltage potential between the first and second power waveforms having first and second phase angles respectively, as a function of time.
Figure 7B:
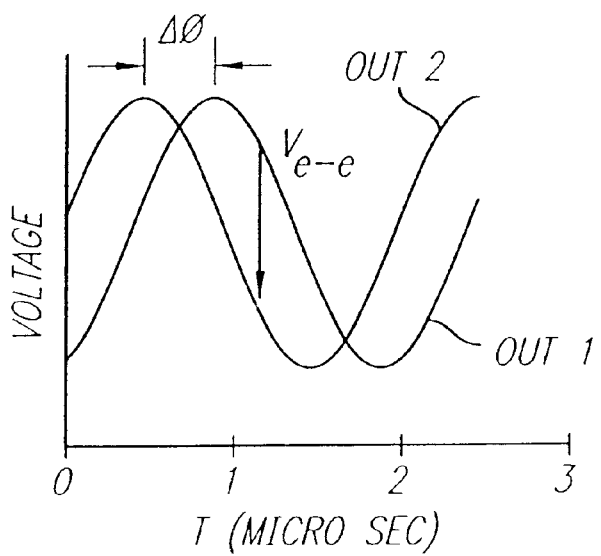
FIG. 7B depicts the phase relationship and voltage potential between the first and second power waveforms having second and first phase angles respectively, as a function of time.

As shown in FIGS. 4, 5, and 6, the two power signals OUT1, OUT2 are phased differently from each other. As discussed above, the phase angle of each power signal is set and controlled by the processor 42 and PLA 60. Each power signal OUT1 and OUT2 has a respective phase angle and those phase angles differ between the two of them. The phase angle difference between the power OUT1 and OUT2 produces a voltage potential between the band electrodes 32 (FIG. 1) hat receive the power. This voltage potential, in turn, induces current flow between the band electrodes 32. The phase angle relationship of the power and the voltage potential produced as a function of time is shown in FIGS. 7A and 7B. The potential between electrodes $V_{e-e}$ is defined by:

$$V_{e-e} = 2V \sin\left(\frac{\Delta\Phi}{2}\right)\sin(2\pi ft) \quad \text{(Eq. 1)}$$

where:
ΔΦ=phase angle difference between electrodes
V=voltage amplitude of power
f=frequency in hertz
t=time FIG. 7A shows first and second power OUT1 and OUT2 provided to first and second electrodes respectively having a phase angle difference ΔΦ with OUT1 leading OUT2 by 132 degrees. FIG. 7B shows the same power OUT1 and OUT2 but with the phase angles reversed where OUT2 is now leading OUT1 by 132 degrees.

Figure 8C:
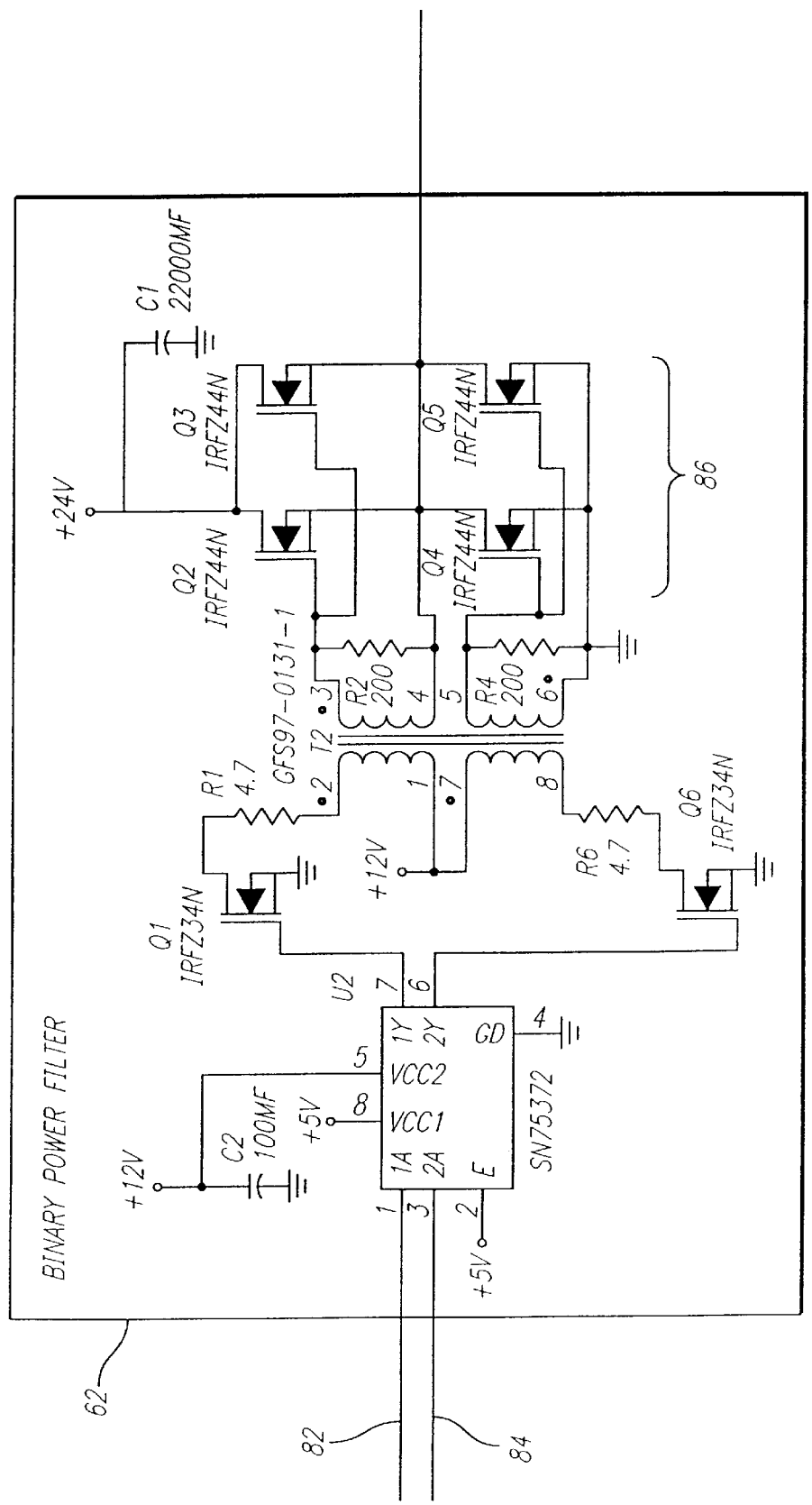
Figure 8D:
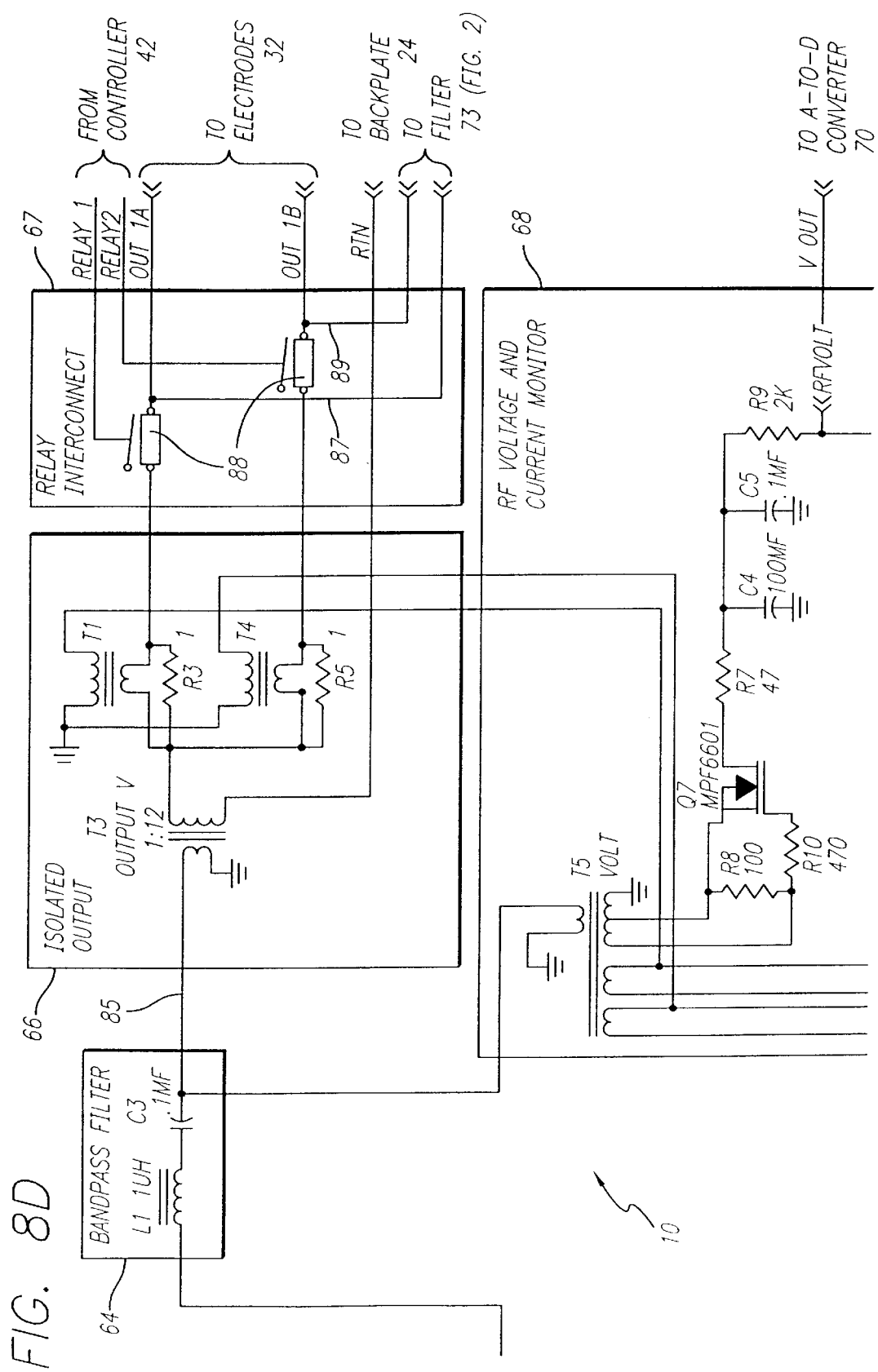
Figure 8E:
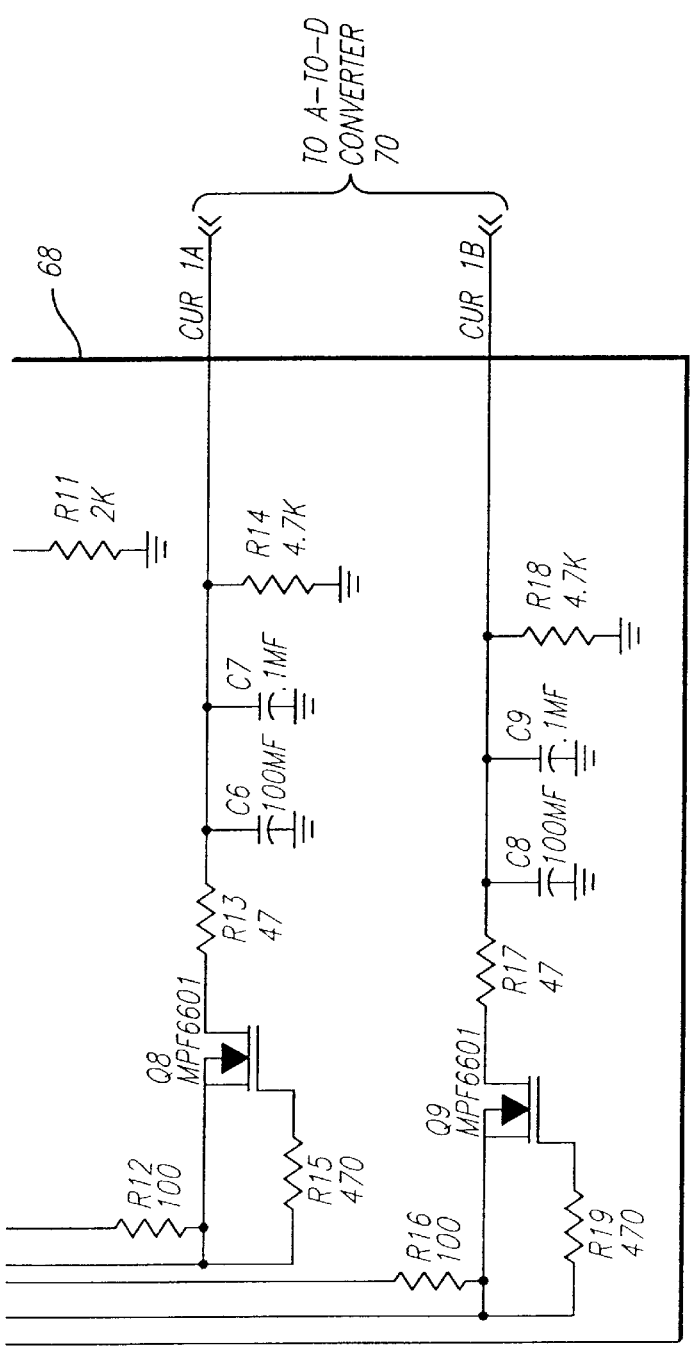
Figure 9A:
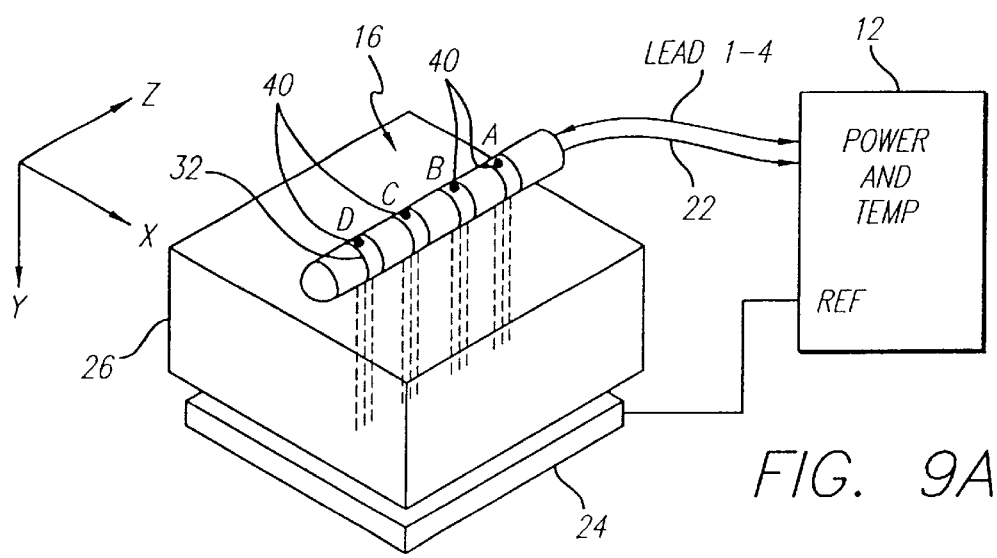
FIG. 9A is a three dimensional representation of an ablation apparatus having a linear array of band electrodes in contact with a biological site with a backplate at the opposite side of the biological site, in which the phase angle difference between adjacent electrodes of the linear array is zero degrees.
Figure 9B:
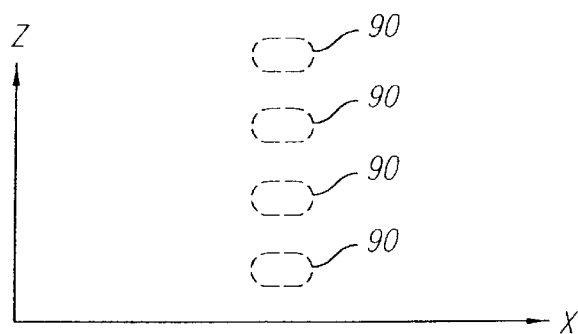
FIGS. 9B through 9D depict, along the x, y, and z axes shown, the depth of the lesions formed by the ablation apparatus of FIG. 9A showing that the apparatus acts as a unipolar device with multiple electrodes and the resulting lesions are discontinuous.
Figure 9C:
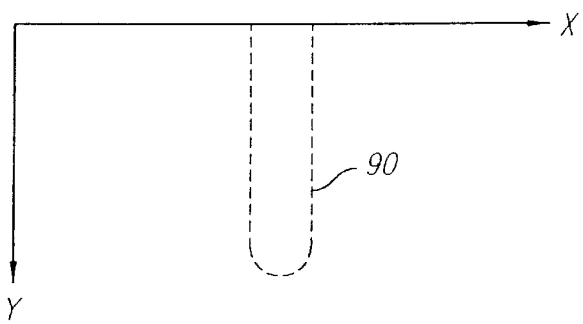
Figure 9D:
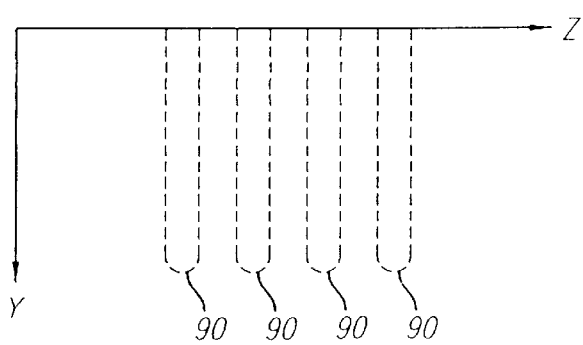

With reference now to FIGS. 8A through 8E, schematic diagrams of an embodiment of the ablation apparatus 10 of FIG. 2 are presented in FIGS. 8B through 8E while FIG. 8A shows how FIGS. 8B through 8E should be oriented in relation to each other. The frequency source 54 provides a signal 80, typically at 500 kHz with a phase angle controlled by the microprocessor 42 through the PLA 60, to the duty cycle generator 45. The duty cycle generator 45 modulates the frequency source signal 80 to produce the selected duty cycle in accordance with the duty cycle control signal 44 as previously described. The duty cycle generator 45 outputs two signals 82 and 84 to the binary power amplifier 62. A dual MOSFET driver U2 receives the signals, converts their 5V level to a 12V level, and sends each to a transformer T2 which transforms the signals into 24 V peak-to-peak power.

The 24V power is then sent to a multi-state driver 86 which includes a configuration of FETs Q2, Q3, Q4, and Q5. During a conducting state of the driver 86, which is typically the on period 74 of the power, these FETs Q2 through Q5 conduct and forward the power to a bandpass filter 64 comprising a series LC network. During a high-impedance state of the driver 86, which is typically during the off period 76 of the power, the FETs Q2 through Q5 are nonconducting and no power is sent to the bandpass filter 64. Instead the FETs Q2 through Q5 present a high impedance load to any signals received through the electrode 32. Typically the load impedance on the FETs Q2 through Q5 presented by the circuit following the FETs , the electrode, and the tissue is approximately 150Ω but transformed through the output transformer T3, it presents a load impedance to the FETs Q2–Q5 of approximately 0.5 to 1Ω. In the off state, the FETs present an impedance of approximately 250Ω which is large in comparison to the transformed load impedance of approximately 0.5 to 1Ω. Therefore, very little power flows when the FETs are in the off state.

The bandpass filter 64 operates to shape the output signal provided by the binary amplifier 62 from a square wave to a sinusoidal wave. The filtered signal 85 then passes to the isolated output section 66 where it is step-up transformed to 350 volt peak-to-peak sinusoidal power at T3. The power is then split into two identical power signals OUT1A, OUT1B and provided to two or more respective band electrodes 32 on the output lines LEAD1A, LEAD1B.

The isolated output section 66 also includes relays 88 that may be individually opened to remove the power signals OUT1A, OUT1B from the electrode leads LEAD 1A, LEAD 1B when an alert condition is detected, such as high temperature or high impedance at the respective electrode 32. As previously mentioned these conditions are determined by the microprocessor 42 which receives signals indicative of the temperature and impedance at each of the band electrodes 32.

The power from the isolated output section 66 is monitored and representative signals are supplied to an RF voltage and current monitor 68 where in this case, the voltage and current of each output signal are measured to determine the impedance of the particular channel. The measured signals are sent to an A-to-D converter 70 (FIG. 2-2) before being sent to the microprocessor 42 for impedance monitoring. If the impedance is above a threshold level indicative of blood clotting or boiling, the microprocessor 42 sends a signal to the duty cycle generator 45 to reduce or discontinue the duty cycle of the power OUT1A, OUT1B and thus lower the effective power delivered to the band electrodes 32.

Similarly, the temperature at the electrodes 32 is determined by monitoring the power 14 and temperature signals 22 and measuring the voltage difference between the signals. As previously mentioned, in one embodiment of the invention, these signals pass through a filter 73 (FIG. 2-2) before being sent to the microprocessor 42. The voltage value is converted to a temperature and if the temperature is above a threshold level the duty cycle of the power 14 is reduced. In the case where a single lead is used to provide a signal which is used to determine the temperature as well as provide power to the electrode 32, the signal from the lead is received on temperature leads 87, 89 connected at the output side of the relays 88.

As shown in FIG. 3, the duty cycle of each electrode 32 may be individually controlled by the microprocessor 42. As previously mentioned, based on the temperature at an electrode 32 and the current and voltage of the output signal provided to an electrode, the duty cycle of the output signal may be adjusted. For example, one electrode 32 may have a temperature requiring a duty cycle of ten percent, while another electrode may have a temperature which allows for a fifty percent duty cycle. In an embodiment in which every other electrode 32 has a temperature sensor 40, the electrodes are grouped in pairs with each electrode in the pair having the same duty cycle.

In operation, as depicted in FIGS. 9A through 11D, the electrode device 16 and the backplate 24 are positioned proximal the biological site 26 undergoing ablation such that the biological site is interposed between the electrode device and the backplate. The band electrodes 32 (only one of which is indicated by a numeral 32 for clarity of illustration) of the electrode device 16 each receives power OUT1, OUT2, OUT3, OUT4 having a phase angle on LEAD 1 through LEAD 4. In one embodiment, every other electrode 32 receives the same phase angle. Therefore, the phase angle of electrode A equals the phase angle of electrode C and the phase angle of electrode B equals the phase angle of electrode D. The advantages of this arrangement are described below. In a preferred embodiment, the electrodes 32 are formed into a linear array as shown. In addition, a thermocouple temperature sensor 40 is located at each of the electrodes A, B, C, and D and uses the electrode power lead LEADS 1 through 4 as one of the sensor leads. The sensors 40 provide temperature sensor signals 22 for receipt by the power control system 12.

In another embodiment, alternate electrodes 32 may be grouped together and each may receive the same power having the same phase angle and duty cycle. Another group or groups of electrodes 32 may be interspaced with the first group such that the electrodes of one group alternate with the electrodes of the other group or groups. Each electrode 32 in a particular group of electrodes has the same phase angle and duty cycle. For example, electrodes A and C may be connected to the same power while interspaced electrodes B and D may be connected to a different power output signal.

The use of individual power signals also provides the ability to disable any combination of electrodes 32 and thereby effectively change the length of the electrode device 16. For example, in one configuration of the present invention an electrode device 16 with twelve electrodes 32 receives twelve power signals from a twelve channel power control system 12. The electrodes 32 are 3 mm in length and are 4 mm apart. Accordingly, by disabling various electrodes, a virtual electrode of any length from 3 mm to 8 cm may be produced by the electrode device 16. In either arrangement the backplate 24 is maintained at the reference voltage level in regard to the voltage level of the power OUT1 through OUTn.

As previously described, by varying the phase angles between the power OUT1, OUT2 supplied to each electrode 32, a phase angle difference is established between adjacent band electrodes. This phase angle difference may be adjusted to control the voltage potential between adjacent band electrodes 32 and thus to control the flow of current through the biological site 26. The flow of current $I_{e-e}$ between adjacent band electrodes 32 is defined by:

$$I_{e-e} = \frac{2V \sin\left(\frac{\Delta\Phi}{2}\right)\sin(2\pi ft)}{Z_{e-e}} \qquad \text{(Eq. 2)}$$

where:
$\Delta\Phi$=phase angle difference between electrodes
V=voltage amplitude of power
$Z_{e-e}$=impedance between electrodes
f=frequency in hertz
t=time In addition to the current flow between the band electrodes 32 there is current flow between the band electrodes and the backplate 24. When the backplate 24 is set at the reference level, this current flow $I_{e-b}$ is defined by:

$$I_{e-b} = \frac{V \sin(2\pi ft)}{Z_{e-b}} \qquad \text{(Eq. 3)}$$

where:
$\Delta\Phi$=phase angle difference between electrodes
V=voltage amplitude of power
$Z_{e-b}$=impedance between electrode and backplate
f=frequency in hertz
t=time Assuming $Z_{e-b}$ and $Z_{e-e}$ are equal, the ratio of the current flowing between the band electrodes 32 $I_{e-e}$ to the current flowing between the band electrodes 32 and the backplate 24 $I_{e-b}$ is defined by:

$$\frac{I_{e-e}}{I_{e-b}} = 2\sin\left(\frac{\Delta\Phi}{2}\right) \qquad \text{(Eq. 4)}$$

where:
$\Delta\Phi$=phase angle difference between electrodes

FIGS. 9A through 11D illustrate various current flow patterns within a biological site. The depths and widths of the lesions depicted in FIGS. 9A through 11D are not necessarily to scale or in scalar proportion to each other but are provided for clarity in discerning the differences between the various power application techniques. When the phase difference between adjacent electrodes 32 is zero degrees, no current flows between the electrodes in accordance with Eq. 2 above, and the apparatus operates in a unipolar fashion with the current flowing to the backplate 24 as shown in FIGS. 9A through 9D. Substantially all current flows from the band electrodes 32 to the backplate 24 forming a series of relatively deep, acute lesions 90 along the length of the electrode device 16. As seen in the top view of FIG. 9B and the side view of FIG. 9D, the lesions are discrete. The lesions 90 are discontinuous in regard to each other.

Figure 10A:
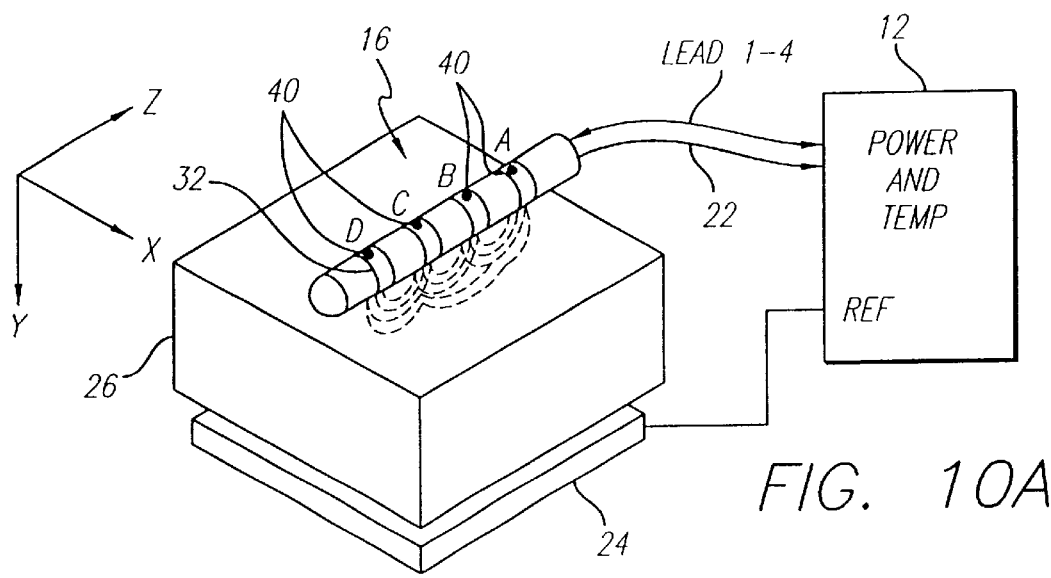
FIG. 10A is a three dimensional representation of an ablation apparatus having a linear array of band electrodes in contact with a biological site with a backplate at the opposite side of the biological site, in which the phase angle difference between adjacent electrodes is 180 degrees.
Figure 10B:
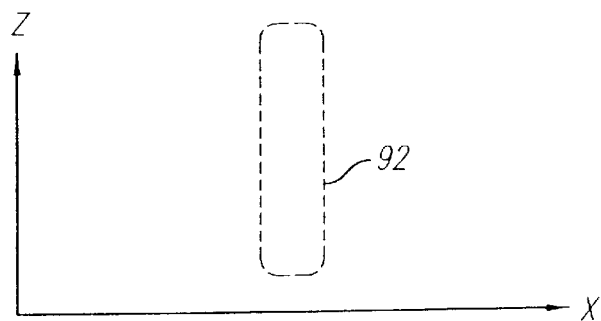
FIGS. 10B through 10D depict, along the x, y, and z axes shown, the continuity and depth of a lesion formed by the ablation apparatus of FIG. 10A showing that the apparatus acts as a bipolar device with no significant amount of current flowing to the backplate.
Figure 10C:
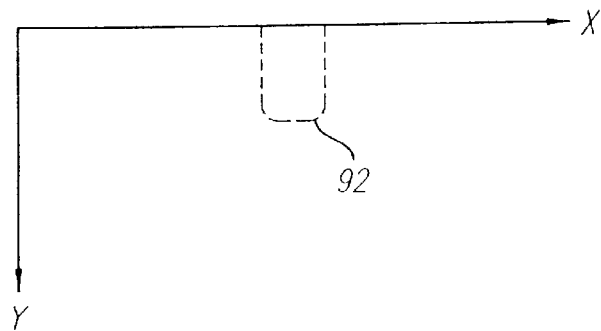
Figure 10D:
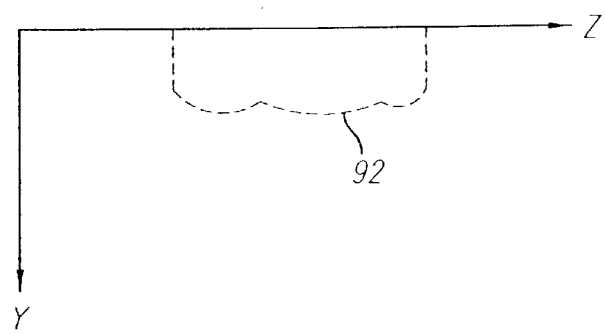

When the phase difference between adjacent electrodes 32 is 180 degrees the apparatus operates in both a unipolar and bipolar fashion and the current flow pattern is as shown in FIG. 10A. With this phase difference, approximately twice as much current flows between adjacent band electrodes 32 than flows from the band electrodes to the backplate 24. The resulting lesion 92 is shallow but is continuous along the length of the electrode device 16. The continuity and shallow depth of the lesion 92 are illustrated in FIGS. 10B through 10D. Nevertheless, the lesion depth is still greater than that created by prior bipolar ablation methods alone.

Figure 11A:
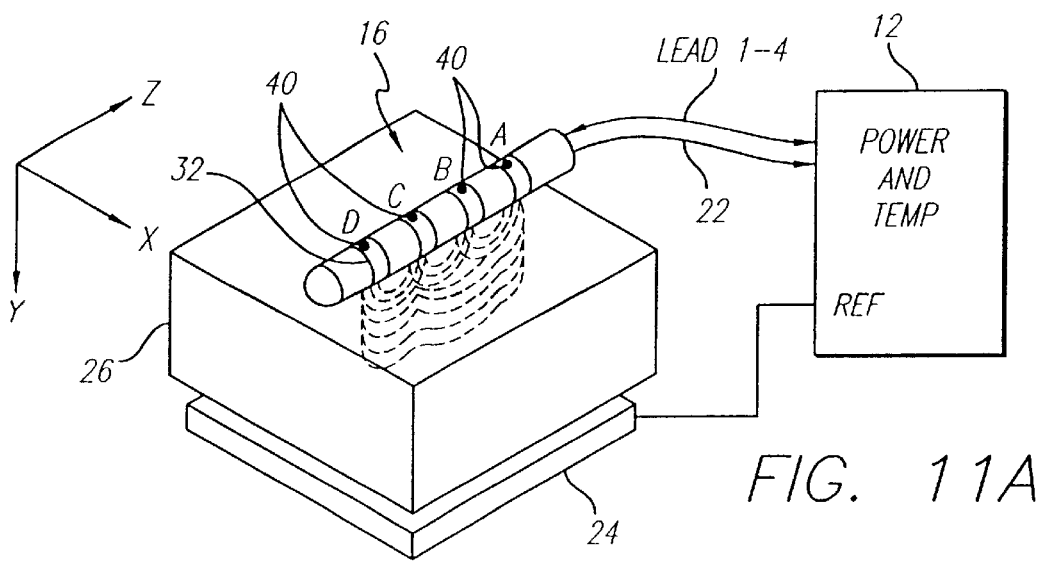
FIG. 11A is a three dimensional representation of an ablation apparatus having a linear array of band electrodes in contact with a biological site with a backplate at the opposite side of the biological site, in which the phase difference between adjacent electrodes is approximately 90 degrees.
Figure 11B:
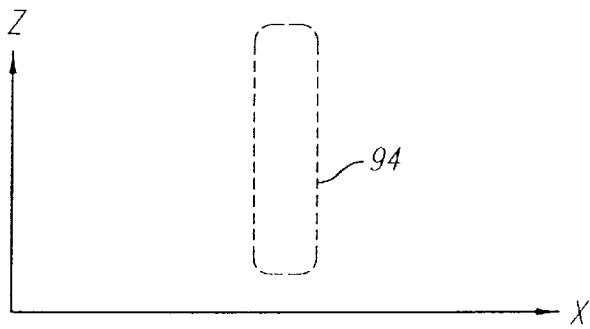
FIGS. 11B through 11D depict, along the x, y, and z axes shown, the continuity and depth of a lesion formed by the ablation apparatus of FIG. 11A showing the greater depth of lesion resulting from the phase angle difference.
Figure 11C:
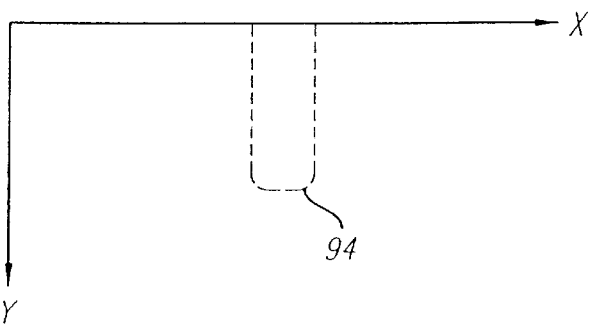
Figure 11D:
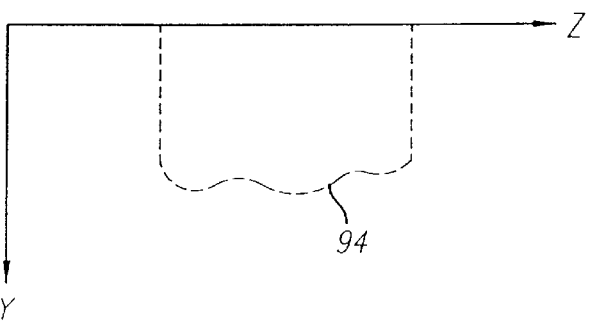

When the phase difference between adjacent electrodes 32 is set within the range of a value greater than zero to less than 180 degrees, the current flow varies from a deep, discontinuous unipolar pattern to a more continuous, shallow bipolar pattern. For example, when the phase difference between adjacent electrodes 32 is around 90 degrees, the current flows as shown in FIG. 11A. With this phase difference, current flows between adjacent band electrodes 32 as well as between the band electrodes and the backplate 24. Accordingly, a lesion which is both deep and continuous along the length of the electrode device 16 is produced. The continuity and depth of the lesion 94 is illustrated in FIGS. 11B through 11D. In one embodiment of FIG. 11A, adjacent electrodes alternated in phase but were provided with power in groups. Electrodes A and C were provided with power at a first phase angle and electrodes B and D were provided with power at a second phase angle, different from the first.

Thus, in accordance with the present invention the phase angle of the power may be adjusted in order to produce a lesion having different depth and continuity characteristics. In selecting the phase angle difference necessary to produce a continuous lesion having the greatest possible depth, other elements of the electrode device 16 are considered. For example, the width of the band electrodes 32 and the spacing between the electrodes are factors in selecting an optimum phase angle. In a preferred embodiment of the present invention, as pointed out above, the width of the band electrodes is 3 mm, the spacing between the electrodes is 4 mm and the electrodes receive power which establish a phase difference of 132 degrees between adjacent electrodes. With this configuration a long continuous lesion having a length of between approximately 3 mm and 8 cm and a depth of 5 mm or greater was produced depending on the number of electrodes energized, the duty cycle employed, and the duration of power application.

In another embodiment of the invention, energy is applied to the biological tissue 26 during the on period of the duty cycle in an alternating unipolar-bipolar manner. During the unipolar mode segment a voltage potential is established between the electrodes 32 and the backplate 24. Thus current flows through the tissue 26 between the electrodes 32 and the backplate 24.

During the bipolar mode segment a voltage potential is established between at least two of the electrodes 32 rather than between the electrodes and the backplate 24. Thus current flows through the tissue 26 between the electrodes 32. While operating in this mode the voltage difference between the electrodes 32 may be established by providing power with different phase angles to the electrodes as previously mentioned. Alternatively, some of the electrodes 32 may be connected to a reference potential while others are maintained at a different voltage level.

By adjusting the duration of the unipolar and bipolar mode segments within the on period of the duty cycle, the continuity and depth of the lesion produced may be controlled. For example, operating in the unipolar mode for one-fourth of the on period and in the bipolar mode for three-fourths of the on period produces a lesion having a continuity and depth similar to the lesion 94 illustrated in FIGS. 11B through 11D.

Referring to FIGS. 8B through and 8E, the following devices are shown:

| Device | Part No. | Manufacturer |
| --- | --- | --- |
| U1 | GAL6002B | Lattice |
| U2 | SN75372 | numerous |
| Q1 | 1RFZ34N | numerous |
| Q2, Q3, Q4, Q5 | 1RFZ44N | numerous |
| Q7, Q8, Q9 | MPF6601 | numerous |
| R3, R5 | 1Ω | numerous |
| T1, T4 | CMI-4810 | Corona Magnetics, Inc. |

-continued

| Device | Part No. | Manufacturer |
| --- | --- | --- |
| T2 | GFS97-0131-1 | GFS Manufacturing |
| T5 | CMI-4809 | Corona Magnetics, Inc. |

The transformer denoted by "T3" is a 1:12 turns ratio, single turn primary, step up transformer wound on a TDK core PC50EER23Z.

The band electrodes 32 generate a heating pattern in the tissue by transmitting RF power into the tissue. The power supplied to the band electrodes 32 is typically increased in order to increase the ablation volume until either an impedance change is noticed due to the onset of clotting or the temperature limit set for the electrode is reached. When one or both of these conditions exist the effective power delivered to the band electrodes 32 is reduced by reducing the duty cycle of the power in this embodiment.

The band electrodes 32 are designed to heat a volume of tissue to an ablation temperature while at the same time assuring that the peak temperature of the band electrodes is controlled so that clotting does not foul the electrode surface and blood boiling does not occur. To this end, each of the band electrodes 32 is formed from a material having a high thermal conductivity. In one embodiment, that material comprised pure platinum. In addition, the band electrodes 32 are sized so that a large surface area is available for contact with the fluid in the heart for dissipating heat to the fluid around the electrode and thereby cooling the electrode. Also, the thickness of the band electrodes 32 is selected so that the electrodes effectively draw heat energy away from the target issue for cooling purposes without unduly increasing the outside diameter of the electrode device.

In accordance with the present invention, with reference to FIGS. 12, 13 and 14, a first electrically conductive member or "leg" 100 and second electrically conductive member or "leg" 102, are connected independently to the band electrode 32 at first and second junctions 104, 106, respectively which are separated from each other. These two electrically conductive members 100, 102 form the wires, i.e., or "legs" of a thermocouple pair. Because of the separation between the locations at which the first and second legs are attached to the inside surface of the band electrode, the part 126 of the band electrode 32 between the connection points 104 and 106 becomes part of the thermocouple and, in effect, serves as a large thermocouple bead 126.

A third conductive member or "leg" 108 is electrically connected to the second leg 102 at a reference junction 110. A voltmeter 112 is disposed across the first leg 100 and the third leg 108 to measure the voltage developed in the thermocouple. In order to correct for extraneous voltage due to dissimilar metal junctions at the voltmeter terminals, the third leg 108 is preferably made of the same material as the first leg 100. The reference junction 110 and the leads for use in connection to the voltmeter are located in the handle 109 of the catheter and are therefore outside the patient.

Conductive members 100 and 108 are connected to a voltmeter 112 located within the controller 20 (FIG. 1). The voltmeter 112 (FIG. 12) provides voltage readings which are related to the temperatures at the various junctions 104, 106, and 110. If the band electrode is heated uniformly, then the temperature reading provided by the two legs will be correct. However, if the temperature of the band electrode is nonuniform, then the voltage output from the two legs will depend upon the local temperatures at the two leg/band contact points and upon the Seebeck coefficients for the two junctions (leg material A/band material and leg material B/band material). The resulting voltage output $V_{ab}$ measured by a voltmeter 112 is expressed by the following general equation:

$$V_{ab}=\alpha_{ac}(T_a-T_{ref})-\alpha_{bc}(T_b-T_{ref}) \quad \text{(Eq. 5)}$$

where:

$\alpha_{ac}$=Seebeck coefficient for the first leg 100 material and the band material $\alpha_{bc}$=Seebeck coefficient for the second leg 102 material and the band material $T_a$=temperature at the first leg 100/electrode junction 104

$T_b$=temperature at the second leg 102/electrode junction 106

$T_{ref}$=temperature at the reference junction 110

$T_{ref}$ and the two Seebeck coefficients, $\alpha_{ac}$ and $\alpha_{bc}$, are typically known for the system at hand. As mentioned briefly above, the reference junction 110 is a controlled temperature junction which is normally included in order to correct for extraneous voltages due to dissimilar metal junctions at the voltmeter terminals. By being located in the handle, for example, the temperature is known to be room temperature, or approximately 22 degrees C. (72 degrees F.). In addition, the Seebeck coefficients are assumed to be constant over the range of temperatures typically encountered in cardiac ablation.

In the present invention, the materials of the first leg 100 and the second leg 102 are chosen such that their Seebeck coefficients, relative to the band electrode 32 material, are equal in magnitude but opposite in sign ($\alpha_{ac}=-\alpha_{bc}$). For pure platinum band electrodes, the following table provides approximate Seebeck coefficients (averaged over the temperature range of from zero to 100° C.) for a variety of different metals and alloys.

| METAL OR ALLOY | SEEBECK COEFFICIENT (mV/C) vs. PURE PLATINUM |
| --- | --- |
| Bismuth | −0.0734 |
| Constantan | −0.0351 |
| Nickel | −0.0148 |
| Cobalt | −0.0133 |
| Alumel | −0.0129 |
| Mercury | −0.0060 |
| Palladium | −0.0057 |
| Calcium | −0.0051 |
| Gold-chromium | −0.0017 |
| Thorium | −0.0013 |
| Platinum | 0 |
| Alloy 11 | +0.0013 |
| Tantalum | +0.0033 |
| Aluminum | +0.0042 |
| Tin | +0.0042 |
| Lead | +0.0044 |
| Magnesium | +0.0044 |
| Stainless steel, 18-8 | +0.0044 |
| Solder 96.5 Sn/3.5 Ag | +0.0045 |
| Solder 50 Sn/50 Pb | +0.0046 |
| Phosphor bronze | +0.0055 |
| Thallium | +0.0058 |
| Yellow brass | +0.0060 |
| Manganin | +0.0061 |
| Iridium | +0.0065 |
| Copper-beryllium | +0.0067 |
| Indium | +0.0069 |
| Rhodium | +0.0070 |
| Silver | +0.0074 |
| Copper | +0.0076 |
| Zinc | +0.0076 |
| Gold | +0.0078 |
| 60 Ni/24 Fe/16 Cr | +0.0085 |
| Cadmium | +0.0090 |
| Tungsten | +0.0112 |
| Cerium | +0.0114 |
| 80 Ni/20 Cr | +0.0114 |
| Spring steel | +0.0132 |
| Molybdenum | +0.0145 |
| Lithium | +0.0182 |
| Iron | +0.0189 |
| Chromel P | +0.0281 |
| Antimony | +0.0489 |

From this table, it is apparent that a variety of suitable wire pairs can be selected. In order to increase the voltage output and improve temperature measurement resolution, Seebeck coefficients of large magnitude are preferred.

In one preferred embodiment, the first and second legs 100 and 102 of the thermocouple are pure nickel and pure molybdenum, which have nearly balanced Seebeck coefficients. These legs 100, 102 are connected to a band electrode 32 of pure platinum.

Figure 15:
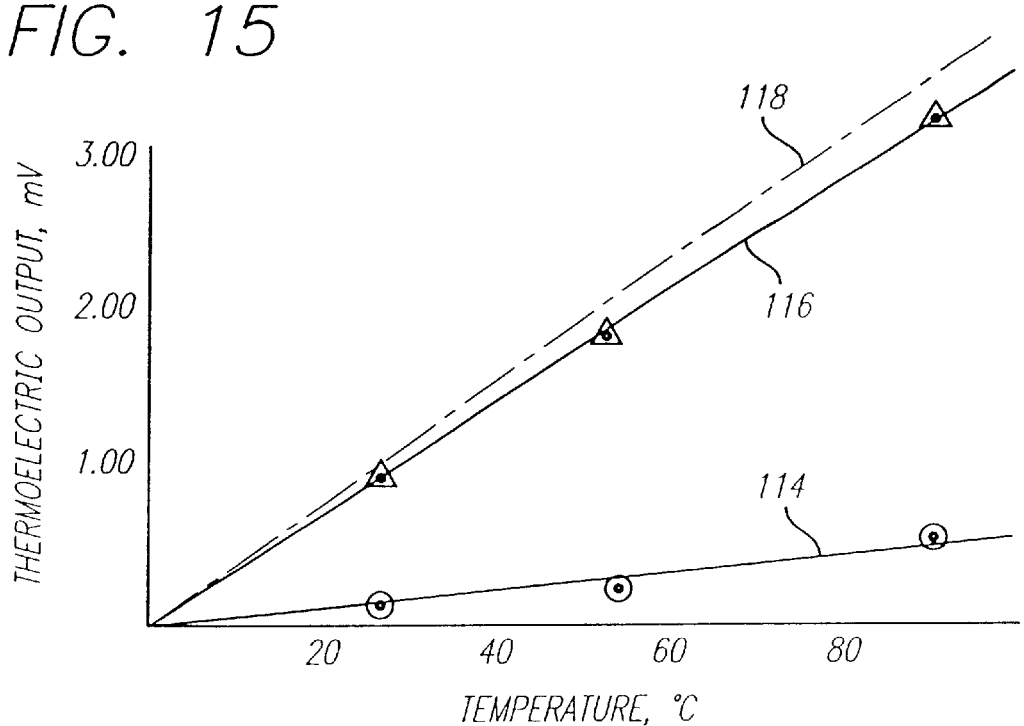
FIG. 15 is a graph showing measured voltage vs. temperature of the thermocouple wire/band electrode/thermocouple wire junctions for a configuration of FIG. 12 having copper and constantan legs, measurements were taken with one junction heated to a target temperature and the other junction held at a fixed temperature of 0° C.

FIG. 15 shows measured voltage vs. temperature for each thermocouple/band electrode junction when one junction is heated to a target temperature and the other junction is held at a fixed temperature (0° C.). In this thermocouple, the first and second legs 100, 102 of the thermocouple are pure constantan and pure copper respectively and are connected to a band electrode 32 of pure platinum. Line 114 represents the thermoelectric output of a copper/platinum junction 104 when heated, while the constantan/platinum junction 106 is maintained at 0° C. in an ice bath. Line 116 represents the thermoelectric output of the constantan/platinum junction 106 when heated, while the copper/platinum junction 104 is maintained at 0° C. in an ice bath. Line 118 represents the thermoelectric output when both junctions 104 and 106 are heated to the same temperature. The materials chosen for the legs are opposite in sign but are not equal in magnitude. This was done to provide a comparison with a thermocouple configured in accordance with the present invention, as described below and illustrated in FIG. 16.

Figure 16:
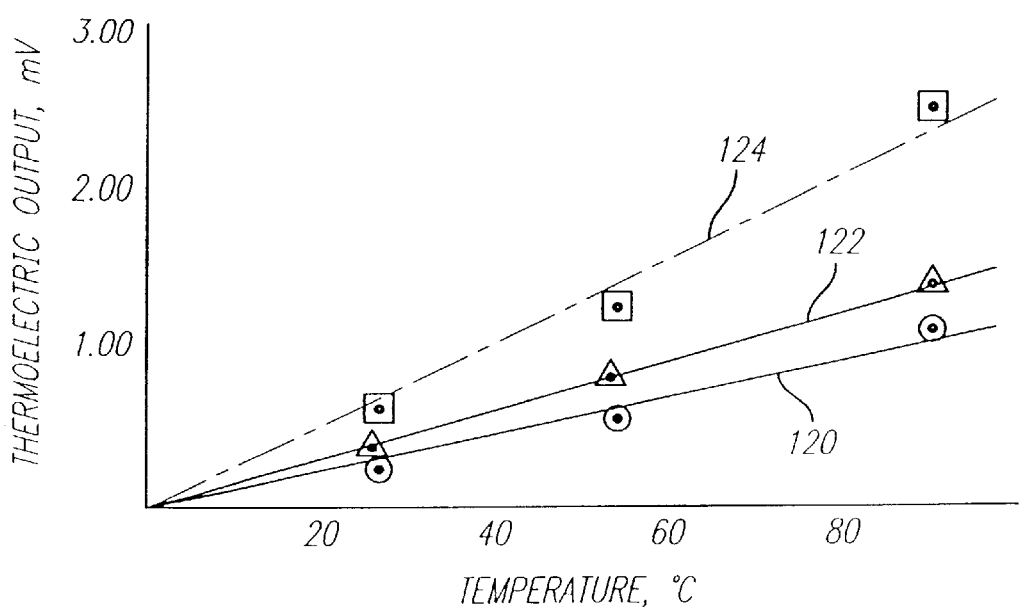
FIG. 16 is a graph showing measured voltage vs. temperature of the thermocouple wire/band electrode/thermocouple wire junctions for a configuration of FIG. 12 having nickel and molybdenum legs, measurements were taken with one junction heated to a target temperature and the other junction held at a fixed temperature of 0° C.

FIG. 16 shows measured voltage vs. temperature for each thermocouple/band electrode junction of a preferred embodiment of the invention when one junction is heated to a target temperature and the other junction is held at a fixed temperature (0° C.). In this embodiment the legs 100, 102 of the thermocouple are pure nickel and pure molybdenum and are connected to a band electrode 32 of pure platinum. Line 120 represents the thermoelectric output of a molybdenum/platinum junction 104 when heated, while the nickel/platinum junction 106 is maintained at 0° C. in an ice bath. Line 122 represents the thermoelectric output of the nickel/platinum-junction 106 when heated, while the nickel/platinum junction 104 is maintained at 0° C. in an ice bath. Line 124 represents the thermoelectric output when both junctions 104 and 106 are heated to the same temperature.

In comparing the graphs of FIGS. 15 and 16, it is shown that for a given temperature in FIG. 15, the thermoelectric output is different depending on which junction is experiencing the higher temperature. For example, if the temperature at the electrode/tissue interface is 80° C. and the junction represented by line 114 is in contact with this interface, the voltmeter detects a voltage of approximately 0.5 mV. If, however, the junction represented by line 116 is in contact with this interface, the voltmeter detects a voltage of approximately 2.75 mV. Thus for the same thermal scenario at the electrode/tissue interface the voltmeter readings are different depending on which junction is at the electrode/tissue interface. To accurately determine the temperature at the interface using such a device, it is necessary to know which junction 104, 106 is located at the interface.

The present invention, however, substantially eliminates the dependency on knowing which junction 104, 106 is located at the electrode/tissue interface.

This is done by choosing legs 100, 102 which have Seebeck coefficients that are equal in magnitude but opposite in sign. As shown in FIG. 16, choosing legs 100, 102 as such produces thermoelectric outputs for a given temperature which remain substantially the same regardless of which junction 104, 106 is located at the electrode/tissue interface. Thus the junctions 104, 106 may be transposed without affecting the reliability of the temperature reading.

As indicated in Eq. 5 the thermoelectric output, i. e., voltage output $V_{ab}$, is related to the two junction temperatures $T_a$ and $T_b$. Using $\alpha_{ab}$ as the net Seebeck coefficient for the two junctions 104, 106 combined, Eq. 5 reduces to:

$$V_{ab} = \alpha_{ac}[(T_a - T_{ref}) + (T_b - T_{ref})] \quad \text{(Eq. 6)}$$
$$= -\alpha_{bc}[(T_a - T_{ref}) + (T_b - T_{ref})]$$
$$= (\alpha_{ab}/2)[(T_a - T_{ref}) + (T_b - T_{ref})]$$
$$= \alpha_{ab}[(T_a + T_b)/2 - T_{ref}]$$

Equation 6 shows that the voltage output is related to the average temperature of the two junctions 104, 106.

During operation of a catheter, depending on the orientation of the band electrode and the positions of the junctions 104, 106 on the band electrode 32, either one, both, or none of the junctions may be located at the electrode/tissue interface. If the band electrode 32 is positioned such that both junctions 104, 106 are located at the electrode/tissue interface, the temperature reading corresponds to the interface temperature. If, however, neither junction 104, 106 is located at the electrode/tissue interface, the temperature corresponds to the temperature of the blood adjacent to the band electrode 32. In either of these situations $T_a$ is substantially equal to $T_b$, i. e., both are the temperature of the electrode/tissue interface or both are the temperature of the local blood pool, and Eq. 6 reduces to:

$$V_{ab} = \alpha_{ab}(T_a - T_{ref}) = \alpha_{ab}(T_b - T_{ref}) \quad \text{(Eq. 7)}$$

If the band electrode 32 is positioned such that one junction 104, 106 is located at or near the electrode/tissue interface, while the other junction 104, 106 is located in the local blood pool the resulting temperature reading is the average of the interface and the known blood temperature. Monitoring the blood temperature ($T_{blood}$) thus permits determination of the temperature of the heated junction $T_a$ or $T_b$ ($T_{junction}$) from the average temperature ($T_{ave}$) using the following equation:

$$T_{junction} = 2(T_{ave}) - T_{blood} \quad \text{(Eq. 8)}$$

A temperature probe placed in appropriate contact with the patient will provide the blood temperature, which in most cases will be 37 degrees C. (98.6 degrees F.). In principle, this value may be manually input to the controller 20 or input directly to the controller from an actual sensor so that the above calculation may be performed automatically.

Figure 17:
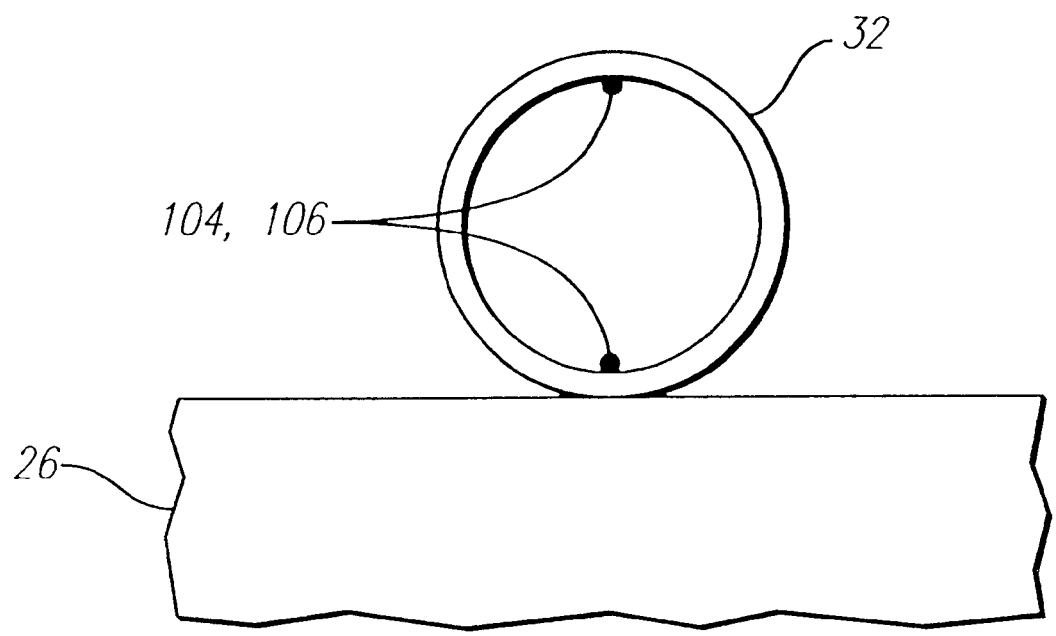
FIG. 17 is a side view of a band electrode having thermocouple legs positioned approximately 180° apart around the circumference of the band electrode in accordance with an aspect of the invention.

In order to determine junction temperature using Eq. 8, it is essential that one of the junctions 104, 106 be located at or near the electrode/tissue interface and the other junction 104, 106 be located in the local blood pool. To this end, the present invention, positions the junctions 104, 106 on the band electrode 32 so that when the electrode is located proximal the biological tissue one of the junctions is positioned at or near the electrode/tissue interface while the other junction is positioned in the biological fluid surrounding the tissue. In a preferred embodiment, the junctions 104, 106 are located on the band electrode approximately 180 degrees apart around the band electrode circumference, as shown in FIG. 17. The positioning of the junctions in this manner ensures that one of the junctions 104, 106 is located at or near the electrode/tissue contact point substantially independent of the rotational orientation of the catheter. To assist in positioning the electrode 32 at the tissue so that one junction 104, 106 is at the electrode/tissue interface and the other junction is in the surrounding fluid, the distal end of the catheter may be preformed such that a predetermined portion of the catheter surface contacts the biological tissue. This could be done, for example, by preforming the catheter into a curve such that the outer profile of the curve normally lies along the line of tissue contact and orienting one junction on the outer profile and the other junction on the inner profile of the curve. Having the two junctions diametrically opposed, e. g., 180 degrees apart, minimizes the possibility of both junctions contacting the tissue at the same time.

Thus the present invention provides for multiple temperature-sensitive locations, i. e., junctions 104, 106 on the band electrode 32 using only two thermocouple wires 100, 102 as opposed to two thermocouple pairs, i. e., four wires, thus resulting in a considerable saving of space in the ablation catheter. This is accomplished by positioning the junctions 104, 106 such that each experiences different temperatures, one being the temperature of the electrode/tissue interface and the other being the temperature of the local blood pool, and by selecting the thermocouple wire material such that either junction 104, 106 may be located at the electrode/tissue interface.

In FIGS. 13 and 14, a band electrode 32 is shown having a non-joined thermocouple formed at the inside surface of the band from two leads of dissimilar metals 100 and 102. Each lead 100, 102 is separately connected to the band electrode 32 to form the two junctions 104, 106. In one embodiment, as shown in FIG. 13, a separate power lead 128 conducts power to the band electrode 32 to impart ablation energy to the biological target tissue. In another embodiment, as shown in FIG. 14, the first lead 100 is also used to conduct power to the band electrode 32 to impart ablation energy to the biological target tissue. Thus only two leads 100 and 102 are used to power and sense at the band electrode 32 rather than the three leads as used in other embodiments. This can result in a substantial savings in size because of the existence of one-third fewer leads to be housed by the catheter. In the case of the twelve-band catheter described above in conjunction with FIG. 1, instead of the normal thirty six leads required, only twenty four leads would be required should the invention be employed. This is a substantial decrease in the number of internal components for the catheter. The inventor hereby incorporates by reference his pending application No. 09/072,800 entitled "Catheter Having Common Lead for Electrode and Sensor" filed May 5, 1998.

Because the thermocouple voltages are typically on the order of 0.001 mV to 0.10 mV per degree C., the power signals conducted on one thermocouple lead 100 could interfere with the detection of the thermocouple signals generated by the thermocouple. Filtration could be used to separate the DC thermocouple signals from the drive or power signals. In another approach, the controller 20 monitors the leads 100 and 102 for thermocouple signals only during the off-period 76 of the duty cycle 78, for example, as shown in FIG. 6. During this off-period, no power is being applied to the band electrode 32 over the first electrode lead 100 and there is less chance for interference with the thermocouple signals produced by the band electrode 32 and conducted on both leads 100 and 102. Thus, the temperatures may be measured briefly without electrical interference.

It should be appreciated that the invention may also be applied to ablation catheters employing alternate sources of electrical energy for ablation, such as ultrasound or microwave energy. The invention may also be applied to any system in which monitoring temperature is important and where the position of multiple temperature sensors is critical to the accuracy of the measurements.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for providing a signal indicative of a temperature, said apparatus comprising:
    an electrically conductive element formed of a first metallic material;
    a first electrically conductive member formed of second metallic material, the first member connected to the electrically conductive element at a first junction;
    a second electrically conductive member formed of a third metallic material, the second member connected to the electrically conductive element at a second junction; and
    wherein the first, second and third metallic materials are chosen such that when the first and second junctions are at different temperatures a voltage output is produced across the electrode proportional to the temperature difference between the two junctions.

2. The apparatus of claim 1 wherein the first and second junctions are spaced apart on the electrically conductive element such that the voltage output is indicative of a temperature which is the average of the first and second junction temperatures.

3. The apparatus of claim 1 wherein the second and third metallic materials are metallic materials having Seebeck coefficients relative to the first metallic material that are substantially equal in magnitude but opposite in sign.

4. The apparatus of claim 1 further comprising:
    a voltmeter for determining the voltage across the first electrically conductive member and the second electrically conductive member; and
    a processor for converting each voltage to a temperature value.

5. An apparatus for collecting temperature data from biological tissue, said apparatus comprising:
    a medical device having an electrically conductive element formed of a first metallic material disposed thereon, the medical device adapted to be positioned so that the electrically conductive element is located proximal the biological tissue;
    a first electrically conductive member formed of second metallic material, the first member connected to the electrically conductive element at a first junction;
    a second electrically conductive member formed of a third metallic material, the second member connected to the electrically conductive element at a second junction; and
    wherein the first, second and third metallic materials are chosen such that when the first and second junctions are at different temperatures a voltage output is produced across the electrically conductive element proportional to the temperature difference between the two junctions.

6. The apparatus of claim 5 wherein the first and second junctions are spaced apart on the electrically conductive element such that the voltage output is indicative of a temperature which is the average of the first and second junction temperatures.

7. The apparatus of claim 5 wherein the first and second junctions are spaced apart on the electrically conductive element such that when the electrically conductive element is located proximal the biological tissue one of the junctions is adapted to be positioned near the electrically-conductive-element/tissue interface while the other junction is adapted to be positioned away from the electrically-conductive-element/tissue interface.

8. The apparatus of claim 5 wherein the electrically conductive element is a band electrode and the first and second junctions are located on the band electrode approximately 180 degrees apart around the band electrode circumference.

9. The apparatus of claim 5 wherein the second and third metallic materials are metallic materials having Seebeck coefficients relative to the first metallic material that are substantially equal in magnitude but opposite in sign.

10. An apparatus for collecting temperature data within a biological structure in which biological fluids flow past the tissue, said apparatus comprising:
    a catheter having a plurality of band electrodes formed of a first metallic material, the band electrodes disposed at a distal end of the catheter, the distal end adapted to be positioned so that at least one of the band electrodes is located proximal the biological tissue;
    a plurality of first electrically conductive members formed of second metallic material, for each of the plurality of band electrodes, one first member connected to the electrode at a first junction; and
    a plurality of second electrically conductive members formed of a third metallic material, for each of the plurality of band electrodes, one second member connected to the electrode at a second junction, wherein the first, second and third metallic materials are chosen such that when the first and second junctions are at different temperatures a voltage output is produced across the electrode proportional to the temperature difference between the two junctions.

11. The apparatus of claim 10 wherein the first and second junctions are spaced apart on each band electrode such that the voltage output is indicative of a temperature which is the average of the first and second junction temperatures of that band electrode.

12. The apparatus of claim 10 wherein the first and second junctions are spaced apart on each band electrode such that when the band electrode is located proximal the biological tissue one of the junctions is adapted to be positioned near the electrode/tissue interface while the other junction is adapted to be positioned in the biological fluid.

13. The apparatus of claim 10 wherein the first and second junctions are located on the band electrode approximately 180° apart around the band electrode circumference.

14. The apparatus of claim 10 wherein the second and third metallic materials are metallic materials having Seebeck coefficients relative to the first metallic material that are substantially equal in magnitude but opposite in sign.

15. A method for collecting temperature data from biological tissue, the biological tissue located in a biological structure in which fluids flow past the tissue, said method comprising the steps of:

positioning a medical device proximal the biological tissue, the medical device having an electrically conductive element formed of a first metallic material and first and second electrically conductive members connected to the electrically conductive element at a first junction and a second junction, respectively, the first and second electrically conductive members being formed of second and third metallic materials, respectively, such that when the two junctions are at different temperatures, a voltage output is produced across the electrically conductive element proportional to the temperature difference between the two junctions, the first and second electrically conductive members being spaced apart on the electrically conductive element;

positioning the electrically conductive element against the tissue so that a portion of the electrically conductive element is available for contact with the fluids in the biological structure; and measuring the voltage output across the electrically conductive element as an indication of a temperature which is the average of the two junction temperatures.

16. The method of claim 15 further comprising the steps of:

placing the first junction in contact with the biological tissue and the second junction in contact with the biological fluid;

measuring the temperature of the biological fluid; and determining the temperature of the first junction from the average temperature.

17. The method of claim 15 wherein the electrically conductive element is a band electrode and the method further comprises the steps of:

placing the first junction in contact with the biological tissue and the second junction approximately 180 degrees away from the first junction around the band electrode circumference;

measuring the temperature of the biological fluid; and determining the temperature of the first junction from the average temperature.

18. The method of claim 15 wherein the second and third metallic materials are metallic materials having Seebeck coefficients relative to the first metallic material that are substantially equal in magnitude but opposite in sign.

* * * * *

UNITED STATES PATENT AND TRADEMARK OFFICE
CERTIFICATE OF CORRECTION

| | | |
|---|---|---|
| PATENT NO. | : 6,440,129 B1 | Page 1 of 1 |
| APPLICATION NO. | : 09/502196 | |
| DATED | : August 27, 2002 | |
| INVENTOR(S) | : John A. Simpson | |

It is certified that error appears in the above-identified patent and that said Letters Patent is hereby corrected as shown below:

Column 9, line 64, change "("BPA")", to read -- ("BPF") --.

Column 11, line 58, change "FIG. 2", to read -- FIGS. 2-1 and 2-2 --.

Signed and Sealed this

Twenty-fifth Day of December, 2007

JON W. DUDAS
*Director of the United States Patent and Trademark Office*